United States Patent
Manley et al.

(10) Patent No.: US 11,547,463 B2
(45) Date of Patent: Jan. 10, 2023

(54) SMOKE EVACUATION ELECTROSURGICAL PENCIL WITH ADJUSTABLE ELECTRODE AND VENT TUBE

(71) Applicant: COVIDIEN LP, Mansfield, MA (US)

(72) Inventors: Prakash Manley, Arvada, CO (US); James D. Allen, IV, Broomfield, CO (US); Tyler J. Bagrosky, Arvada, CO (US); Conor N. Byrne, Traverse City, MI (US); Jason T. Sanders, Longmont, CO (US); Chelsea E. Walbridge, Longmont, CO (US); Chandler E. Lacy, Centennial, CO (US)

(73) Assignee: COVIDIEN LP, Mansfield, MA (US)

( * ) Notice: Subject to any disclaimer, the term of this patent is extended or adjusted under 35 U.S.C. 154(b) by 505 days.

(21) Appl. No.: 16/565,150

(22) Filed: Sep. 9, 2019

(65) Prior Publication Data
US 2020/0093535 A1  Mar. 26, 2020

Related U.S. Application Data

(60) Provisional application No. 62/734,397, filed on Sep. 21, 2018.

(51) Int. Cl.
*A61B 18/14* (2006.01)
*A61B 18/00* (2006.01)
(Continued)

(52) U.S. Cl.
CPC .......... *A61B 18/1402* (2013.01); *A61B 18/14* (2013.01); *A61B 2018/00083* (2013.01);
(Continued)

(58) Field of Classification Search
CPC ......... A61B 18/1402; A61B 2218/008; A61M 39/1055; F16L 27/0849; F16L 27/0853; F16L 27/0861; F16L 27/04
See application file for complete search history.

(56) References Cited

U.S. PATENT DOCUMENTS

| 4,347,842 A | 9/1982 | Beale |
| 4,562,838 A | 1/1986 | Walker |

(Continued)

FOREIGN PATENT DOCUMENTS

WO    2012155922 A2    11/2012

OTHER PUBLICATIONS

Australian Examination Report No. 1, dated May 17, 2017, corresponding to Australian Application No. 2012388657; 4 pages.
(Continued)

*Primary Examiner* — Joanne M Hoffman
*Assistant Examiner* — Sean W Collins
(74) *Attorney, Agent, or Firm* — Carter, DeLuca & Farrell LLP

(57) ABSTRACT

An electrosurgical smoke evacuation pencil includes a handle housing having a proximal end portion and a distal end portion, the handle housing defining a first lumen therethrough. The electrosurgical pencil also includes a nozzle disposed within the first lumen and defining a second lumen, the nozzle being movable relative to and within the handle housing and extending proximally past the proximal end portion of the handle housing. The electrosurgical pencil may further include a swivel connector coupled to the distal end portion of the handle housing, the swivel connector configured to couple to a suction source. The electrosurgical pencil includes a hub assembly securedly disposed within the second lumen, the hub assembly including a conductive tube configured to couple to a source of electrosurgical energy, and an electrode slidably disposed within the conductive tube, the electrode being movable relative to and within the conductive tube.

19 Claims, 12 Drawing Sheets

(51) Int. Cl.
  *A61B 90/00* (2016.01)
  *A61M 39/10* (2006.01)

(52) U.S. Cl.
  CPC .............. *A61B 2018/00178* (2013.01); *A61B 2018/00184* (2013.01); *A61B 2018/00196* (2013.01); *A61B 2018/00607* (2013.01); *A61B 2018/00916* (2013.01); *A61B 2018/00928* (2013.01); *A61B 2018/1412* (2013.01); *A61B 2018/1422* (2013.01); *A61B 2018/1425* (2013.01); *A61B 2018/1475* (2013.01); *A61B 2090/034* (2016.02); *A61B 2217/005* (2013.01); *A61B 2218/008* (2013.01); *A61M 39/1055* (2013.01)

(56) References Cited

U.S. PATENT DOCUMENTS

| | | |
|---|---|---|
| 4,676,241 A | 6/1987 | Webb et al. |
| 4,683,884 A | 8/1987 | Hatfield et al. |
| 4,719,914 A | 1/1988 | Johnson |
| 4,850,352 A | 7/1989 | Johnson |
| 4,856,822 A * | 8/1989 | Parker ................ F16L 27/0861 285/94 |
| 4,911,159 A | 3/1990 | Johnson et al. |
| 4,919,129 A | 4/1990 | Weber, Jr. et al. |
| 5,013,300 A | 5/1991 | Williams |
| 5,035,695 A | 7/1991 | Weber, Jr. et al. |
| 5,071,418 A | 12/1991 | Rosenbaum |
| 5,085,657 A | 2/1992 | Ben-Simhon |
| 5,108,389 A | 4/1992 | Cosmescu |
| 5,154,709 A | 10/1992 | Johnson |
| 5,181,916 A | 1/1993 | Reynolds et al. |
| 5,192,267 A | 3/1993 | Shapira et al. |
| 5,197,963 A | 3/1993 | Parins |
| 5,199,944 A | 4/1993 | Cosmescu |
| 5,234,428 A | 8/1993 | Kaufman |
| 5,242,442 A | 9/1993 | Hirschfeld |
| 5,318,516 A | 6/1994 | Cosmescu |
| 5,318,565 A | 6/1994 | Kuriloff et al. |
| 5,348,555 A | 9/1994 | Zinnanti |
| 5,360,427 A | 11/1994 | Majlessi |
| 5,413,575 A | 5/1995 | Haenggi |
| 5,431,650 A | 7/1995 | Cosmescu |
| 5,449,357 A | 9/1995 | Zinnanti |
| 5,451,222 A | 9/1995 | De Maagd et al. |
| 5,451,223 A | 9/1995 | Ben-Simhon |
| 5,460,602 A | 10/1995 | Shapira |
| 5,479,019 A | 12/1995 | Gross |
| 5,496,314 A | 3/1996 | Eggers |
| D373,190 S | 8/1996 | Monson |
| 5,554,172 A | 9/1996 | Horner et al. |
| 5,578,000 A | 11/1996 | Greff et al. |
| 5,593,406 A | 1/1997 | Eggers et al. |
| 5,609,573 A | 3/1997 | Sandock |
| D384,148 S | 9/1997 | Monson |
| 5,674,219 A | 10/1997 | Monson et al. |
| 5,681,262 A | 10/1997 | Isse |
| 5,693,044 A | 12/1997 | Cosmescu |
| 5,707,402 A | 1/1998 | Heim |
| 5,797,901 A | 8/1998 | Cosmescu |
| 5,800,431 A | 9/1998 | Brown |
| 5,830,214 A | 11/1998 | Flom et al. |
| 5,836,909 A | 11/1998 | Cosmescu |
| 5,836,944 A | 11/1998 | Cosmescu |
| 5,935,125 A | 8/1999 | Zupkas |
| 5,951,548 A | 9/1999 | DeSisto et al. |
| 5,968,042 A | 10/1999 | Emster |
| 6,099,525 A | 8/2000 | Cosmescu |
| 6,120,498 A | 9/2000 | Jani et al. |
| 6,142,995 A | 11/2000 | Cosmescu |
| 6,149,648 A | 11/2000 | Cosmescu |
| 6,210,323 B1 | 4/2001 | Gilhuly et al. |
| 6,258,088 B1 | 7/2001 | Tzonev et al. |
| 6,287,305 B1 | 9/2001 | Heim et al. |
| 6,293,945 B1 | 9/2001 | Parins et al. |
| 6,355,034 B2 | 3/2002 | Cosmescu |
| 6,364,853 B1 | 4/2002 | French et al. |
| 6,451,017 B1 | 9/2002 | Moutafis et al. |
| 6,458,125 B1 | 10/2002 | Cosmescu |
| 6,524,307 B1 | 2/2003 | Palmerton et al. |
| 6,533,781 B2 | 3/2003 | Heim et al. |
| 6,558,379 B1 | 5/2003 | Batchelor et al. |
| 6,602,249 B1 | 8/2003 | Stoddard et al. |
| 6,616,658 B2 | 9/2003 | Ineson |
| 6,635,034 B1 | 10/2003 | Cosmescu |
| 6,702,812 B2 | 3/2004 | Cosmescu |
| 6,899,712 B2 | 5/2005 | Moutafis et al. |
| 6,918,902 B2 | 7/2005 | French et al. |
| 7,033,353 B2 | 4/2006 | Stoddard et al. |
| 7,083,601 B1 | 8/2006 | Cosmescu |
| 7,112,199 B2 | 9/2006 | Cosmescu |
| 7,172,592 B2 | 2/2007 | DeSisto |
| 7,303,559 B2 | 12/2007 | Peng et al. |
| 7,329,253 B2 | 2/2008 | Brounstein et al. |
| 7,377,919 B2 | 5/2008 | Heim et al. |
| 7,537,594 B2 | 5/2009 | Sartor |
| 7,731,713 B2 | 6/2010 | Christoudias |
| 7,761,188 B2 | 7/2010 | Palmerton et al. |
| 7,828,794 B2 | 11/2010 | Sartor |
| 7,935,109 B2 | 5/2011 | Cosmescu |
| 7,967,816 B2 | 6/2011 | Deel et al. |
| 8,057,470 B2 | 11/2011 | Lee et al. |
| 8,095,241 B2 | 1/2012 | Palmerton et al. |
| 8,109,929 B2 | 2/2012 | Eitenmueller |
| 8,211,103 B2 | 7/2012 | Greep |
| 8,414,576 B2 | 4/2013 | Cosmescu |
| 8,518,018 B2 | 8/2013 | Minskoff et al. |
| 8,690,872 B2 | 4/2014 | Jayaraj |
| 8,702,700 B2 | 4/2014 | Maeda et al. |
| 9,987,074 B2 | 6/2018 | Ineson |
| 2002/0019631 A1 | 2/2002 | Kidder et al. |
| 2002/0058931 A1 | 5/2002 | Parker et al. |
| 2002/0072651 A1 | 6/2002 | Vilos |
| 2002/0103485 A1 | 8/2002 | Melnyk et al. |
| 2003/0088247 A1 | 5/2003 | Ineson |
| 2004/0030328 A1 | 2/2004 | Eggers et al. |
| 2004/0064136 A1 | 4/2004 | Papineau et al. |
| 2004/0260280 A1 | 12/2004 | Sartor |
| 2004/0267326 A1 | 12/2004 | Ocel et al. |
| 2006/0058778 A1 | 3/2006 | Arcusa Villacampa et al. |
| 2006/0264928 A1 | 11/2006 | Komerup et al. |
| 2007/0038213 A1* | 2/2007 | Machiya ............ A61B 18/1492 606/45 |
| 2007/0066970 A1 | 3/2007 | Ineson |
| 2007/0129722 A1 | 6/2007 | Cosmescu |
| 2007/0249990 A1 | 10/2007 | Cosmescu |
| 2008/0103431 A1 | 5/2008 | Brounstein et al. |
| 2008/0163941 A1* | 7/2008 | Lundman .............. F16L 55/124 138/93 |
| 2008/0287893 A1 | 11/2008 | Ineson |
| 2009/0018490 A1 | 1/2009 | Wuchinich |
| 2009/0018539 A1 | 1/2009 | Cosmescu |
| 2009/0062791 A1 | 3/2009 | Lee et al. |
| 2009/0076486 A1 | 3/2009 | Cucin |
| 2009/0192441 A1 | 7/2009 | Gelbart et al. |
| 2010/0094283 A1 | 4/2010 | Cosmescu |
| 2010/0125172 A1 | 5/2010 | Jayaraj |
| 2010/0168745 A1 | 7/2010 | Loeser |
| 2011/0034921 A1 | 2/2011 | Sartor |
| 2011/0077645 A1 | 3/2011 | Lin |
| 2011/0190768 A1 | 8/2011 | Shvetsov et al. |
| 2011/0230878 A1 | 9/2011 | Ryan et al. |
| 2011/0319892 A1 | 12/2011 | Blomeyer |
| 2012/0101497 A1 | 4/2012 | Jayaraj |
| 2012/0203223 A1 | 8/2012 | Terry et al. |
| 2012/0283718 A1 | 11/2012 | Cosmescu |
| 2012/0283728 A1 | 11/2012 | Cosmescu |
| 2013/0006236 A1 | 1/2013 | Greep et al. |
| 2013/0204246 A1 | 8/2013 | Greep et al. |
| 2014/0046413 A1 | 2/2014 | Kane |
| 2014/0081086 A1 | 3/2014 | Shvetsov et al. |
| 2015/0005761 A1 | 1/2015 | Zinnanti |
| 2015/0209100 A1 | 7/2015 | Ineson |

(56) References Cited

U.S. PATENT DOCUMENTS

2015/0335377 A1    11/2015  Brooke
2018/0028255 A1*  2/2018  Miller ................ A61B 18/1402
2018/0092692 A1    4/2018  Cosmescu
2018/0333191 A1*  11/2018  Greep ................... A61B 18/00

OTHER PUBLICATIONS

Australian Examination Report No. 1, dated May 23, 2018, corresponding to Australian Application No. 2014324006; 3 pages.
Canadian Office Action and Examination Search Report dated Sep. 28, 2018, corresponding to Canadian Application No. 2,883,231; 5 total pages.
Australian Examination Report No. 1, dated Mar. 2, 2020, corresponding to counterpart Australian Application No. 2019232833; 7 pages.
Canadian Office Action dated Dec. 7, 2020, issued in corresponding Canadian Appln. No. 3,056,081, 8 pages.

* cited by examiner

SMOKE EVACUATION ELECTROSURGICAL PENCIL WITH ADJUSTABLE ELECTRODE AND VENT TUBE

This application claims the benefit of, and priority to, U.S. Provisional Patent Application No. 62/734,397, filed on Sep. 21, 2018. The entire contents of which is hereby incorporated herein by reference.

BACKGROUND

1. Technical Field

The present disclosure relates to surgical devices. More specifically, the present disclosure relates to handheld smoke evacuation electrosurgical pencils having a telescopic nozzle movable within and relative to a handpiece and a telescopic electrode movable within and relative to the nozzle.

2. Background of Related Art

Electrosurgical (ES) pencils are used in surgery, typically for cutting tissue and/or for coagulating blood vessels. An ES pencil usually includes a handpiece into which electrodes of various shapes and sizes may be placed. The electrode is supplied with a high frequency, typically radio frequency (RF) alternating current provided by an ES generator, such as Medtronic's Valleylab™ LS10 or FT10 Generators. The ES generator may supply various waveforms suitable for achieving various surgical effects, such as cutting, coagulating, blend, spray, fulgurate, and the like.

While using an ES pencil, smoke is often generated. An effective way to evacuate surgical smoke is to use an ES pencil with an integrated smoke evacuation nozzle in conjunction with a suction device and an ultra-low penetration air (ULPA) filter. Conventional ES pencils rely on smoke evacuation shrouds attached to the ES pencil, which suction the smoke away via a suction device. Smoke shrouds are available either as an integrated part of the ES pencil or as a separate shroud attached to the ES pencil. A smoke nozzle, situated near the pencil's electrode, draws the smoke plume into and through the pencil's body, through a long flexible hose, and finally into a powered suction device outside of the surgical field.

During a surgical procedure it is often desirable to change the length of the electrode. Therefore electrodes come in different lengths. However, this results in added expense due to inclusion of multiple electrodes in surgical kits and added surgical time because the surgical procedure needs to be stopped while the electrode is being changed.

SUMMARY

The present disclosure provides an electrosurgical (ES) pencil having an integrated, telescopic smoke nozzle disposed within a handle housing. The ES pencil includes an electrical plug configured to couple to an electrosurgical generator. The handle housing may have an ergonomic shape and have a slim cross-sectional area (e.g., having a height, width, or diameter of from about 10 mm to about 20 mm). The nozzle evacuates surgical smoke through the handle housing and through smoke evacuation tubing into a smoke evacuator. The smoke evacuation tubing may be corrugated to minimize kinking and to allow for free and natural movement of the ES pencil. The nozzle may be clear to aid with visualization of an electrode and its electrode tip. The nozzle also directs the smoke past a printed circuit board (PCB) coupled to a rocker switch to limit alternative current paths that could potentially harm the user due to smoke intrusion into sensitive electronic components. The PCB has an over mold on the front and back of the pencil as well as tape that covers the PCB to limit moisture ingress. A rocker switch is disposed over the PCB and is used to control the energy delivered by the ES pencil by engaging the push-button switches disposed on the PCB.

The extension and retraction force of the nozzle may be controlled by a friction pad that contacts the nozzle. The friction pad may be located within a distal portion of the handle housing, such that the friction pad contacts the nozzle. The ES pencil also includes a high flow swivel connector disposed at a proximal portion of the handle housing. The swivel connector allows the ES pencil and the tubing to rotate independently from each other. The swivel connector allows the tubing to rest in a comfortable position and minimizes the overall weight of the pencil by increasing the amount of tubing that may rest on surgical drapes.

The ES pencil also includes a conductive tube connected to a wire, which is in turn connected to the plug through the PCB, such that the conductive tube conducts electrosurgical current to an electrode from the generator. The electrode and the conductive tube have a non-conductive shrink-wrap or coating that prevents alternative contact sites during surgery. The conductive tube may be secured within the nozzle while the electrode is configured to move within the conductive tube by using an electrode clip that is configured to frictionally slide within the conductive tube.

The present disclosure includes multiple embodiments, each of which includes multiple aspects. Various aspects of the embodiments are interchangeable among the disclosed embodiments. According to one embodiment of the present disclosure, an electrosurgical smoke evacuation pencil is disclosed, which includes: a handle housing having a proximal end portion and a distal end portion, the handle housing defining a first lumen therethrough. The ES pencil also includes a nozzle disposed within the first lumen and defining a second lumen, the nozzle being movable relative to and within the handle housing and extending proximally past the proximal end portion of the handle housing. The ES pencil further includes a swivel connector coupled to the distal end portion of the handle housing, the swivel connector is configured to couple to a suction source. The ES pencil also includes a hub assembly securely disposed within the second lumen, the hub assembly includes a conductive tube configured to couple to a source of electrosurgical energy, and an electrode slidably disposed within the conductive tube, the electrode being movable relative to and within the conductive tube.

According to one aspect of the above embodiment, the ES pencil includes an electrode clip slidably disposed within the conductive tube, the electrode clip being movable relative to and within the conductive tube, where the electrode is removably coupled to the electrode clip.

According to another aspect of the above embodiment, the ES pencil further includes a proximal support disposed over a proximal end portion of the conductive tube and a distal support disposed over a distal end portion of the conductive tube. The proximal support and the distal support may be formed from a dielectric material. The hub assembly may further include a dielectric material disposed over the conductive tube. The dielectric material may be a heat-shrinkable wrap. Each of the proximal support and the distal support may include a pair of flanges configured to secure each of the proximal support and the distal support within the nozzle. The conductive tube may include a proximal stop member and longitudinal movement of the electrode clip is limited by the distal support and the proximal stop member.

According to a further aspect of the above embodiment, the electrode clip may also include a socket configured to receive a proximal end portion of the electrode and a pair of contact wings configured to contact an inner surface of the conductive tube. The electrode clip may include a plurality of prongs disposed at a proximal portion of the electrode clip and a plurality of surface features disposed at a distal portion of the electrode clip, the surface features being configured to contact an inner surface of the conductive tube.

According to one aspect of the above embodiment, the ES pencil may further include a midframe disposed within the handle housing and over the nozzle. The midframe may include a pair of wings configured to frictionally engage the nozzle. The handle housing includes an upper portion having a switch opening and a lower portion. The ES pencil also includes a circuit board including at least one switch and a rocker disposed through the switch opening, the rocker configured to engage the at least one switch.

According to another aspect of the above embodiment, the distal end portion of the handle housing includes a tubular connector. The swivel connector includes a distal joint coupled to the tubular connector and rotatable about a first longitudinal axis defined by the tubular connector. The swivel connector also includes an intermediate joint coupled to the distal joint and pivotable about an axis that is perpendicular to the first longitudinal axis. The swivel connector further includes a proximal joint coupled to the intermediate joint and rotatable about a second longitudinal axis defined by the intermediate joint. The distal joint may include a pair of opposing pins and the intermediate joint may include a pair of opposing openings configured to engage the pair of opposing pins. The distal joint also includes an outer curved surface and the intermediate joint includes an inner curved surface, the outer curved surface includes a raised surface configured to limit pivoting movement of the intermediate joint.

According to one embodiment of the present disclosure, an electrosurgical smoke evacuation pencil is disclosed, which includes a handle housing having a proximal end portion and a distal end portion, the handle housing defining a first lumen therethrough. The ES pencil includes a nozzle disposed within the first lumen and defining a second lumen, the nozzle being movable relative to and within the handle housing and extending proximally past the proximal end portion of the handle housing. The ES pencil also includes a swivel connector coupled to the distal end portion of the handle housing, the swivel connector is configured to couple to a suction source. The ES pencil further includes a hub assembly securedly disposed within the second lumen, the hub assembly including a conductive tube configured to couple to a source of electrosurgical energy. The ES pencil also includes an electrode clip slidably disposed within the conductive tube, the electrode clip being movable relative to and within the conductive tube, and an electrode removably coupled to the electrode clip.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
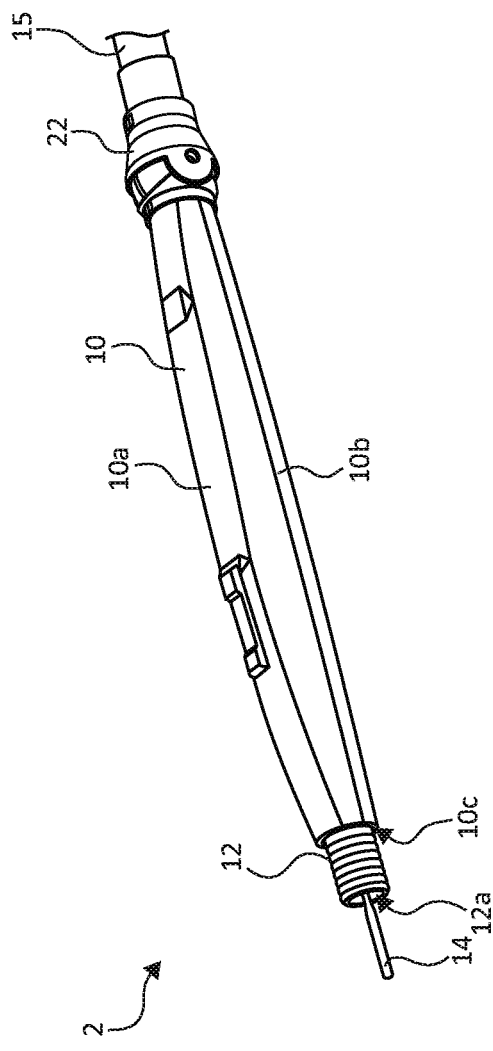
FIG. 1 is a perspective view of a smoke evacuation electrosurgical (ES) pencil according to one embodiment of the present disclosure.

Embodiments of the present disclosure are now described in detail with reference to the drawings in which like reference numerals designate identical or corresponding elements in each of the drawings. The embodiments may be combined in any manner consistent with the functionality of the apparatus and/or method disclosed herein. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. The terms "substantially equal to" or "substantially the same" denote that two values are within ±5% of each other. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure describes multiple embodiments of smoke evacuation electrosurgical (ES) pencils, each of which includes a handle with an integrated smoke nozzle. In embodiments, the nozzle may be telescopic, such that the nozzle is movable relative to and within the handle. Each of the ES pencils also includes an electrode electrically coupled to a conductive tube disposed within the nozzle. The conductive tube may be secured to the nozzle and in certain embodiments, the electrode may also be telescopic, such that the electrode is movable relative to and within the conductive tube, and by extension, the nozzle, while maintaining electrical contact with the conductive tube. The ES pencil may also include a swivel connector coupled to a proximal end of the handle. The swivel connector may include a ball joint, a pivot joint, or combinations thereof. The swivel connector couples the nozzle to a flexible tube, which is in turn connected to a smoke evacuator.

With reference to FIG. 1, a non-telescopic ES pencil 2 is disclosed, which includes a handle housing 10 formed from a thermoplastic material. The handle housing 10 includes an upper portion 10a and a lower portion 10b, which are secured to each other using any suitable methods, e.g., ultrasonically welded, to secure internal components of the ES pencil 2. The handle housing 10 defines a lumen 10c therethrough. The ES pencil 2 also includes a nozzle 12 that is securely coupled within the housing 10, and an electrode 14 disposed within the nozzle 12. The nozzle 12 also defines a lumen 12a, which is in fluid communication with the lumen 10c.

Figure 2:
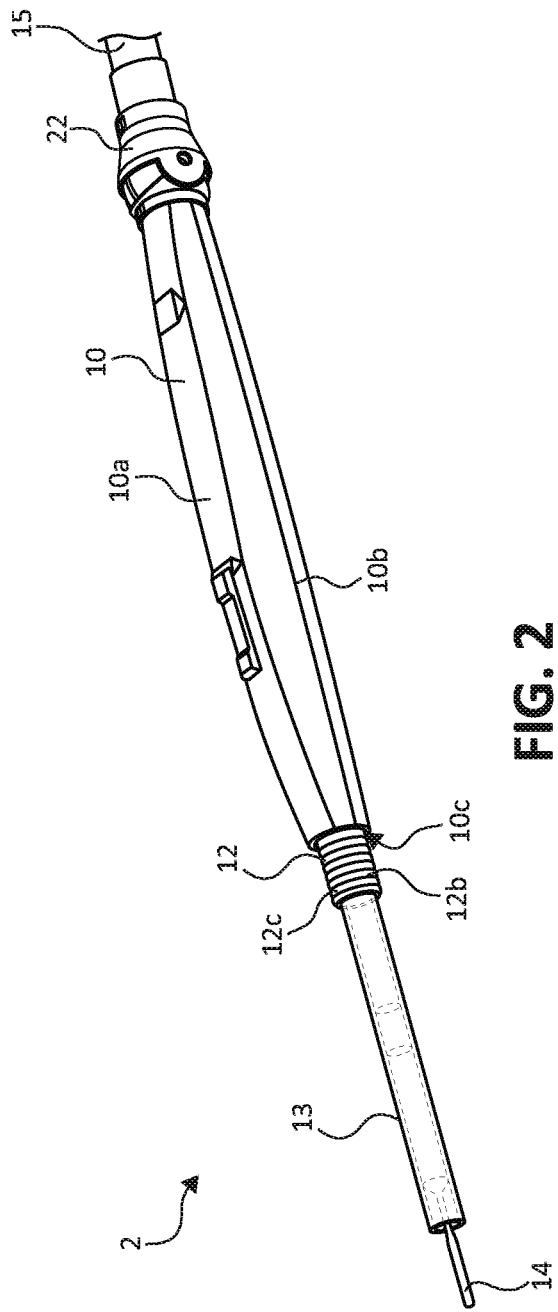
FIG. 2 is a perspective view of the ES pencil of FIG. 1 with a nozzle extender attachment according to the present disclosure.

The nozzle 12 is formed from a dielectric material, such as polyimide, and provides for the suctioning of gaseous byproducts through the handle housing 10. In embodiments, dielectric material of the nozzle 12 may be a transparent, substantially transparent or translucent material configured to facilitate visual acuity in the surgical field. However, it will be clear that an opaque or substantially opaque material may also be used as such materials would not affect the operation of the device. The ES pencil 2 also includes a swivel connector 22 coupling the nozzle 12 to a tubing 15. As shown in FIG. 2 the nozzle 12 may also include a distal end portion 12b, which is configured to couple to a nozzle extender attachment 13. The distal end portion 12b may have a plurality of ribs 12c for frictionally engaging the nozzle extender attachment 13. This allows the ES pencil 2 to have a longer nozzle 12 to use with a longer electrode 14 for deeper access.

Figure 3:
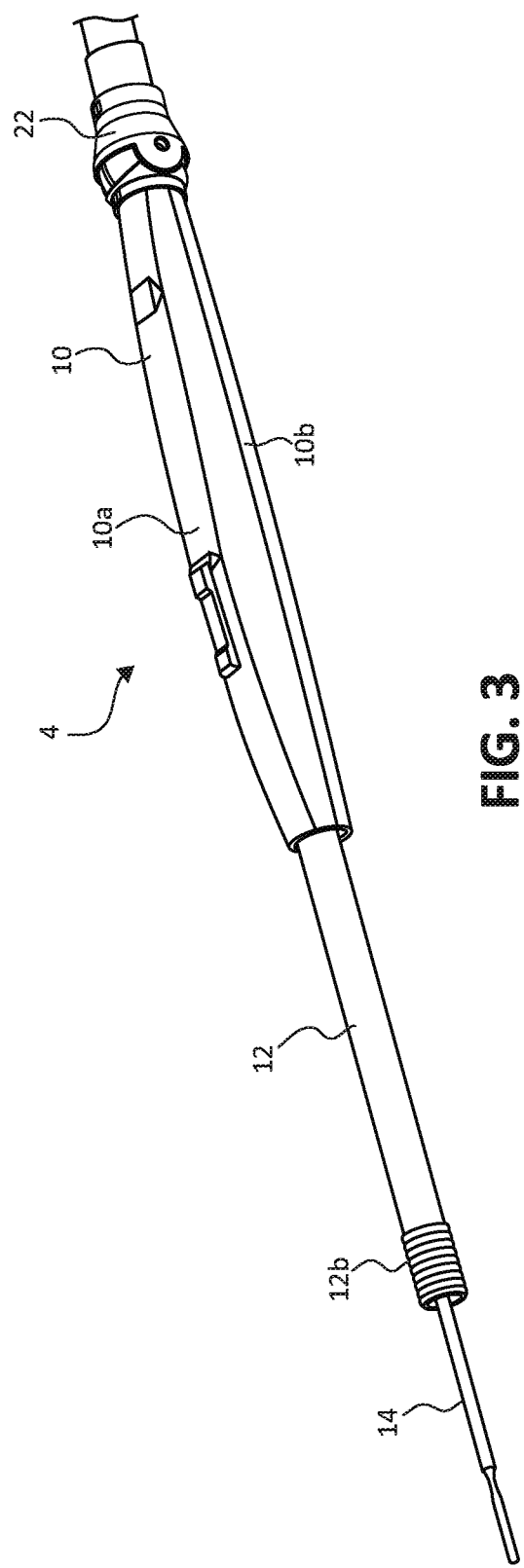
FIG. 3 is a perspective view of a smoke evacuation ES pencil according to another embodiment of the present disclosure.
Figure 4:
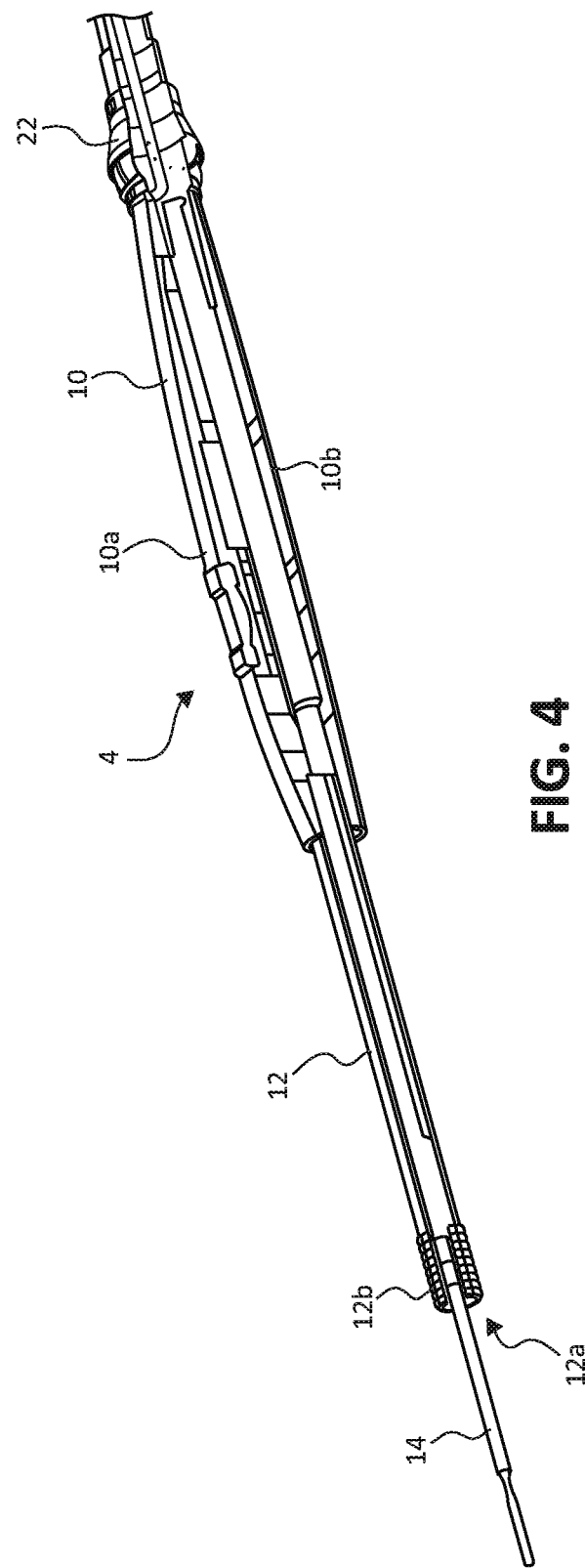
FIG. 4 is a perspective, cross-sectional view of the ES pencil of FIG. 3.
Figure 5:
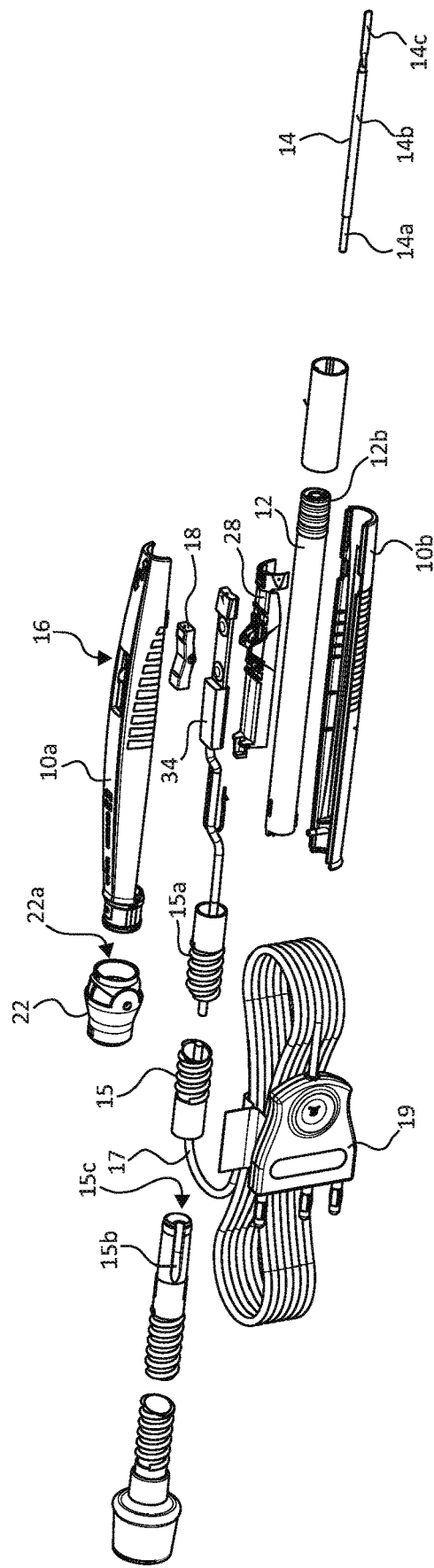
FIG. 5 is a perspective view of the ES pencils of FIGS. 1 and 3, with parts separated.

With reference to FIGS. 3-5, a telescopic ES pencil 4 includes the same components as the ES pencil 2 and is different with respect to its functionality. The ES pencil 4 also includes the housing 10. The ES pencil 4 includes the nozzle 12 that is movable relative to the handle housing 10 and within the lumen 10c. As shown in FIGS. 3 and 4, both the nozzle 12 and the electrode 14 are extended longitudinally. The nozzle 12 also includes the taper portion 12b. The electrode 14 is slidably coupled within the nozzle 12 such that the electrode 14 is movable relative to the nozzle 12. The electrode 14 includes a proximal portion 14a, an insulative coating 14b, and a distal portion 14c having a treatment portion e.g., a blade (as shown), a hook, a needle, etc. (FIG. 5) It is envisioned that other variants of ES pencils 2 and 4 may include either the nozzle 12 or the electrode 14 that are telescopic with the other being stationary, namely, the nozzle 12 is secured to the housing while the electrode 14 is movable and vice versa.

Figure 6:
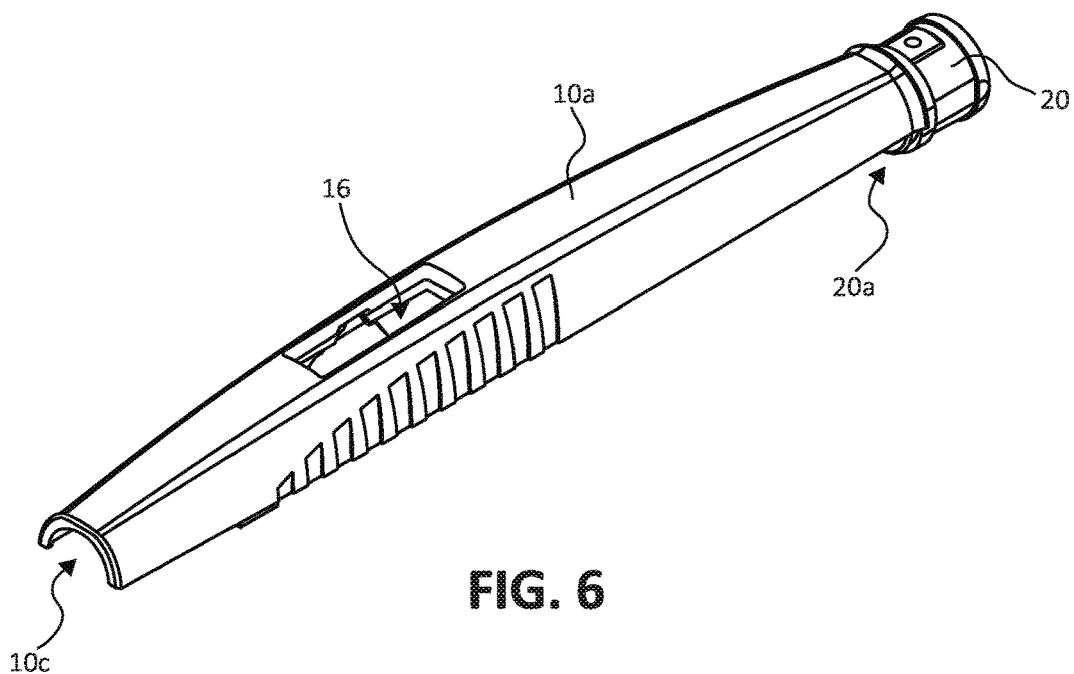
FIG. 6 is a perspective view of an upper portion of a handle housing of the ES pencils of FIGS. 1 and 3.
Figure 7:
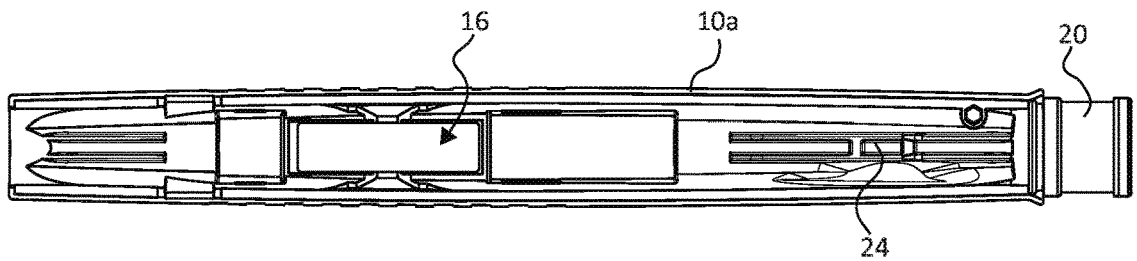
FIG. 7 is an interior view of the upper portion of the handle housing of FIG. 6.

With reference to FIGS. 5-7, the upper portion 10a includes a switch opening 16 that accommodates a rocker switch 18 (FIG. 5). Rocker switch 18 may be replaced by any of suitable actuation mechanism, such as a multistage push button switch, two or more push button switches, a pressure sensitive transducer, or the like. The upper portion 10a also includes a tubular member 20 disposed at a distal end portion for coupling to the swivel connector 22 (FIG. 5). The tubular member 20 defines a lumen 20a, which is in fluid communication with the lumen 10c, allowing for the smoke evacuated from the surgical site to flow from the nozzle 12, through the handle housing 10, and the tubular member 20 to the tubing 15, namely, through the lumens 10c, 12a, and 20a. In embodiments tubular member 20 may be included on bottom portion 10b rather than upper portion 10a.

With reference to FIG. 5, the swivel connector 22 is coupled to the tubing 15, which is configured to couple of a smoke evacuator (not shown). The tubing 15 may be corrugated by including a spiral spine 15a disposed on an outer surface of the tubing 15. The corrugated structure of the tubing 15 minimizes kinking and allows for more flexibility of the tubing 15. The tubing 15 also includes an opening 15b at any point along its length for passage of an electrosurgical cable 17 into a lumen 15c defined within the tubing 15. The cable 17 is coupled to a connector plug 19 for connection to an electrosurgical generator (not shown).

Figure 8:
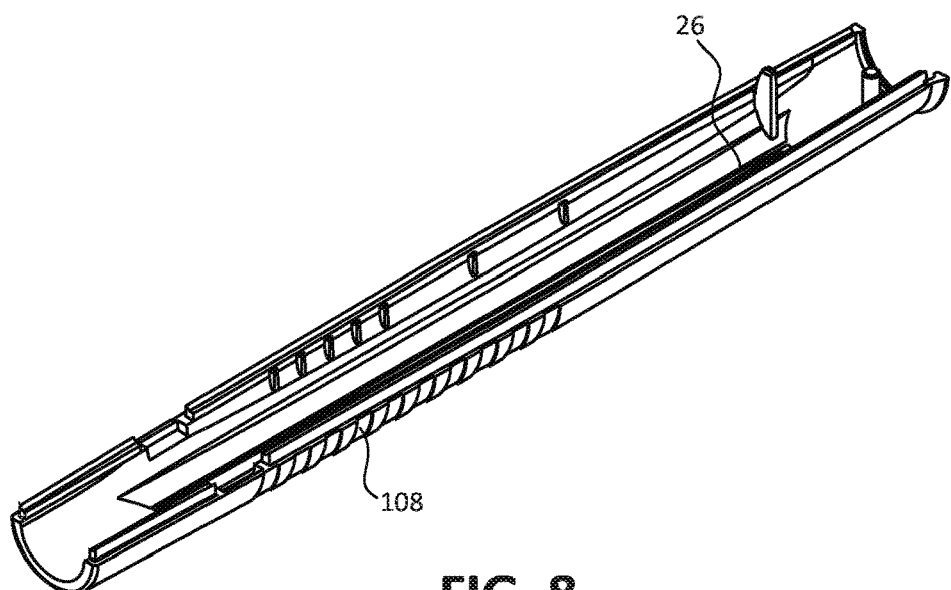
FIG. 8 is a perspective view of a lower portion of a handle housing of the ES pencils of FIGS. 1 and 3.

As shown in FIG. 7, the upper portion 10a also includes a notch 24 formed on an inner surface of the upper portion 10a, which secures the nozzle 12 within the handle housing 10 in the stationary variant of the ES pencils. With reference to FIG. 8, the lower portion 10b includes a guide rail 26 disposed on an inner surface of the lower portion 10b, which allows the nozzle 12 to move within the handle housing 10.

Figure 9:
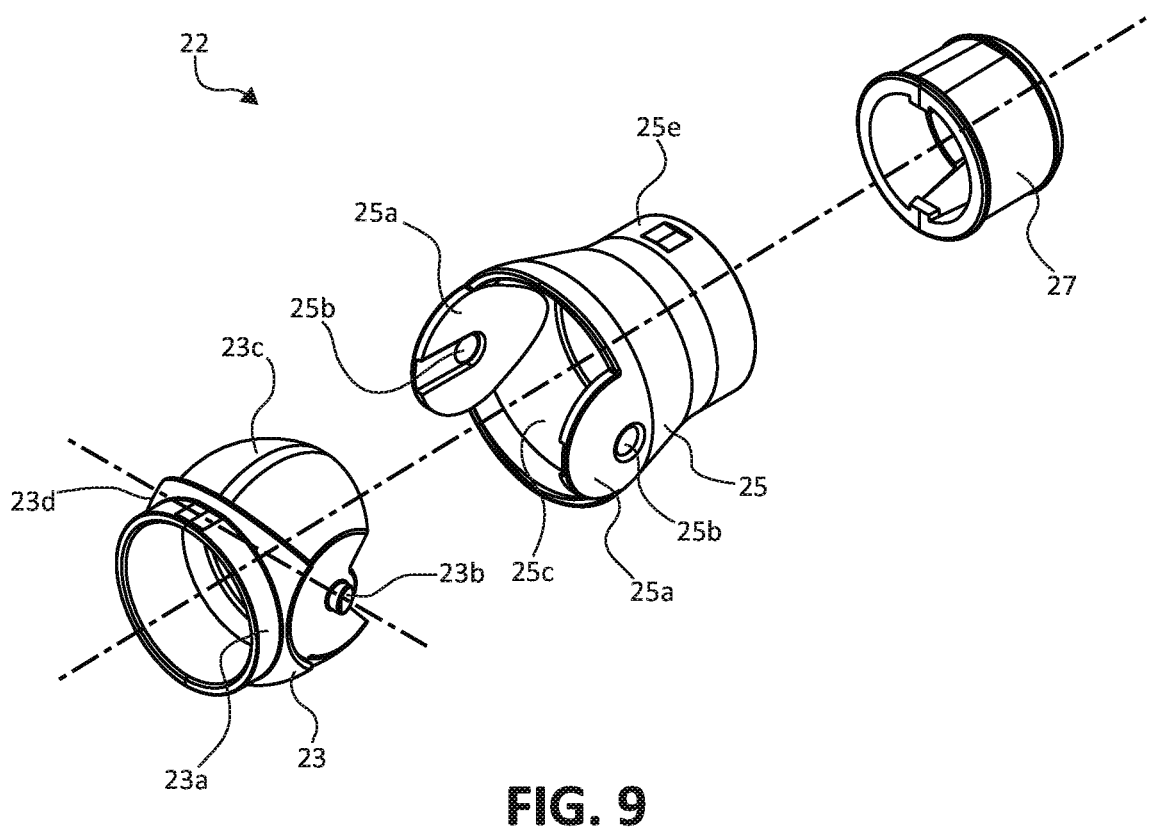
FIG. 9 is a perspective view of a swivel connector of the ES pencils of FIGS. 1 and 3 with parts separated, according to the present disclosure.
Figure 10:
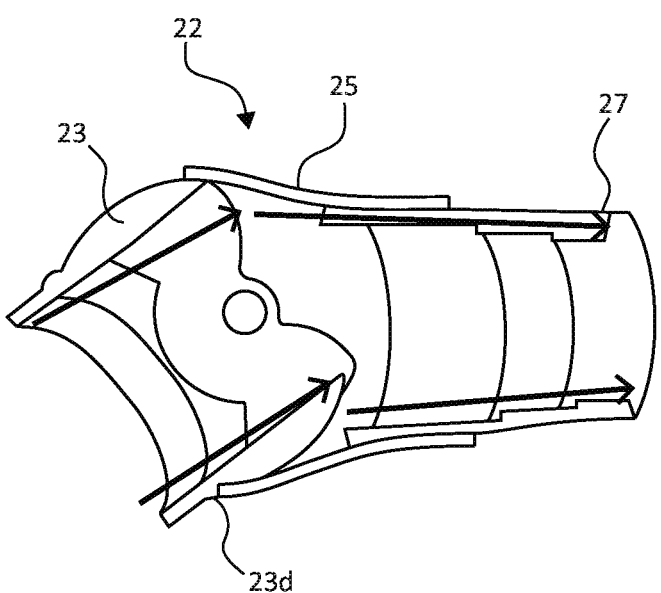
FIG. 10 is a side, cross-sectional view of the swivel connector of FIG. 9.

With reference to FIGS. 9 and 10, the swivel connector 22 includes a distal joint 23, an intermediate joint 25, and a proximal joint 27. The distal joint 23 includes a distal tubular portion 23a configured to engage the tubular member 20 of the upper portion 10a such that the distal joint 23 can rotate about a first longitudinal axis defined by the tubular connector 20. The distal joint 23 also includes a pair of pins 23b (only one is shown) defining a pivot axis perpendicular to the first longitudinal axis. Furthermore, the distal joint 23 includes an outer curved surface 23c extending from a proximal edge to a distal edge having a raised surface 23d.

The intermediate joint 25 includes a pair of wings 25a, each of which includes an opening 25b configured to engage corresponding pins 23b of the distal joint 23. This allows the intermediate joint 25 to pivot relative to the distal joint 23 about the pivot axis. In embodiments, the openings 25b may be disposed on the distal joint 23 and the pins 23b may be disposed on the intermediate joint 25.

The intermediate joint 25 also includes an inner curved surface 25c which is configured to mate with the outer curved surface 23c such that as the intermediate joint 25 moves relative to the distal joint 23 without forming any gaps, which let gases escape therethrough or cause an unintended vacuum leak as shown in FIG. 10. The raised surface 23d of the distal joint 23 limits the rotation of the intermediate joint 25 by acting as a stop member. While pivoting the cross section of a passage through the distal joint 23 and the intermediate joint 25 is maintained because the intermediate joint 25 overlaps the distal joint 23 as illustrated in FIG. 10. Maintaining the same cross-sectional area of the passage allows for a higher flow rate than other swivel joint designs.

The intermediate joint 25 also includes a tubular portion 25e configured to engage the proximal joint 27, which is rotatably coupled to the intermediate joint 25 allowing the proximal joint 27 to rotate about a second longitudinal axis defined by the intermediate joint 25. The proximal joint 27 is also coupled to the tubing 15 at a proximal end of the proximal joint 27. This allows the proximal joint 27 along with the tubing 15 to rotate about the second longitudinal axis. Thus, the swivel connector 22 provides three degrees of freedom, one at each of the distal joint 23 (rotation about the first longitudinal axis), the intermediate joint 25 (pivoting about the pivot axis perpendicular to the first and/or the second longitudinal axes), and proximal joint 27 (rotation about the second longitudinal axis).

Figure 11:
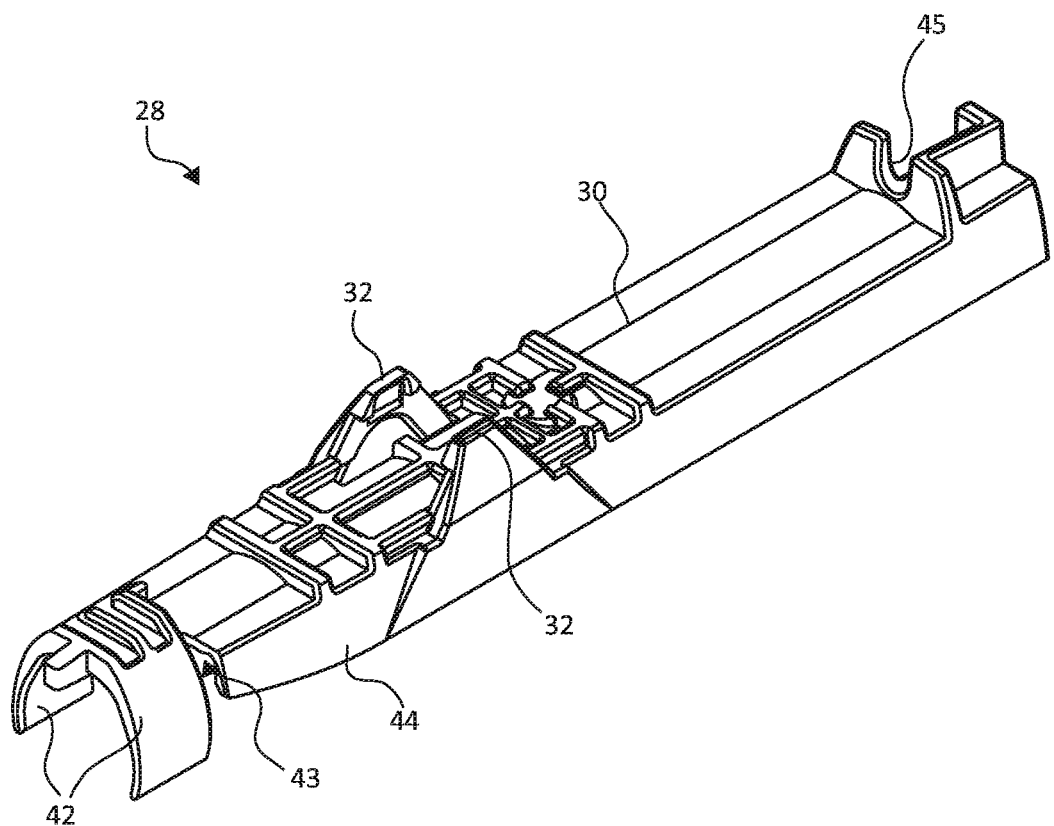
FIG. 11 is a perspective view of a midframe disposed within the handle housing of the ES pencils of FIGS. 1 and 3 according to the present disclosure.

Referring to FIGS. 5 and 11, the ES pencils 2 and 4 also include a midframe 28 that is disposed in the upper portion 10a. As shown in FIG. 5 below, the midframe 28 includes an upper support surface 30 and a pair of tabs 32 extending upwardly from the upper support surface 30. The midframe 28 is disposed over the nozzle 12; as such the smoke evacuated from the treatment site bypasses the midframe 28 and a circuit board 34 disposed thereon. Similarly, in the ES pencil 4, the midframe 28 is disposed over the nozzle 12 and outside the travel path of the nozzle 12.

Figure 12:
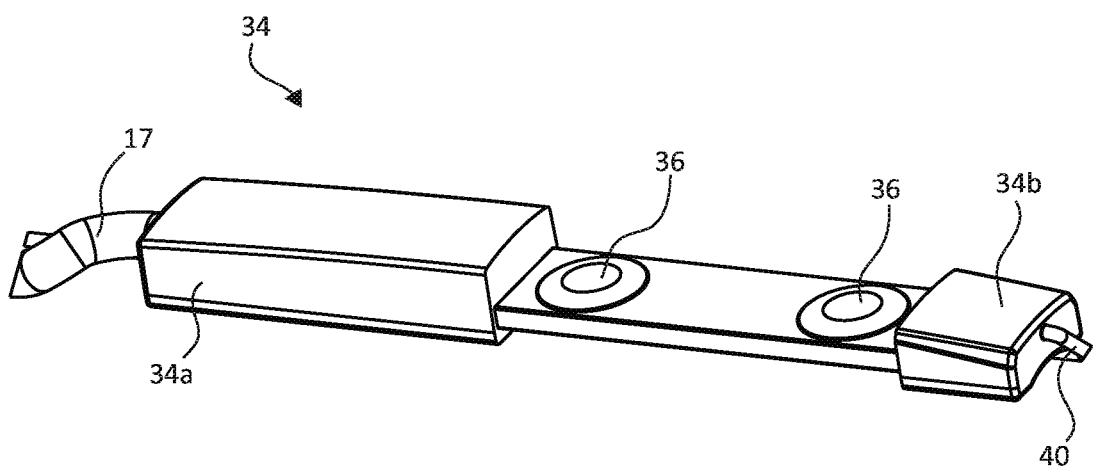
FIG. 12 is a perspective view of a circuit board disposed on the midframe of the ES pencils of FIGS. 1 and 3 according to the present disclosure.

Referring again to FIGS. 5 and 12, the circuit board 34 is disposed on the upper support surface 30 and is secured by the pair of tabs 32. The circuit board 34 includes a pair of pushbutton switches 36, which are aligned with the rocker 18 that is also pivotally secured by the pair of tabs 32 thereby allowing for activation of the pushbutton switches 36 when the rocker 18 is pressed (FIG. 5). The circuit board 34 is coupled at its proximal end portion 34a to the cable 17, which interconnects the circuit board 34 to the electrosurgical generator (not shown). The circuit board 34 is also coupled to an electrode lead 40 at its distal end portion 34b, which interconnects the circuit board 34 to the electrode 14. In embodiments, the connections to the circuit board 34 of the cable 17 and the electrode lead 40 may be reversed, e.g., the electrode lead 40 is coupled to the proximal end portion 34a and the cable 17 is coupled to the distal end portion 34b, or the connections may be coupled to the same end.

The circuit board 34 may be enclosed in a dielectric material to prevent alternative current paths that could potentially harm the user. In embodiments, the circuit board 34 and the pushbutton switches 36 may be wrapped in a heatshrinkable material or dielectric tape such as SURLYN® ionomer resin tape from DuPont of Wilmington, Del. The distal and proximal end portions 38a and 38b may be encased in dielectric material, such as polyimide, epoxies, and the like using any suitable techniques, such as overmolding or casting.

As shown in FIG. 11, the midframe 28 also includes a pair of wings 42 disposed at a proximal end portion and a pair of lips 44 running along the length of the midframe 28. The wings 42 and lips 44 extend downward and are configured to secure the nozzle 12. Additionally, in telescopic ES pencil 4, the wings 42 also act as a friction pad by contacting the nozzle 12 and securing the nozzle 12 within the housing 10 unless sufficient force is used to move the nozzle 12, thereby modulating the amount of force needed to move the nozzle 12 longitudinally. The midframe 28 also includes a cutout 43 disposed between the wings 42 and lips 44 for routing the electrode lead 40 and another cutout 45 at the distal end portion for routing the cable 17.

Figure 13:
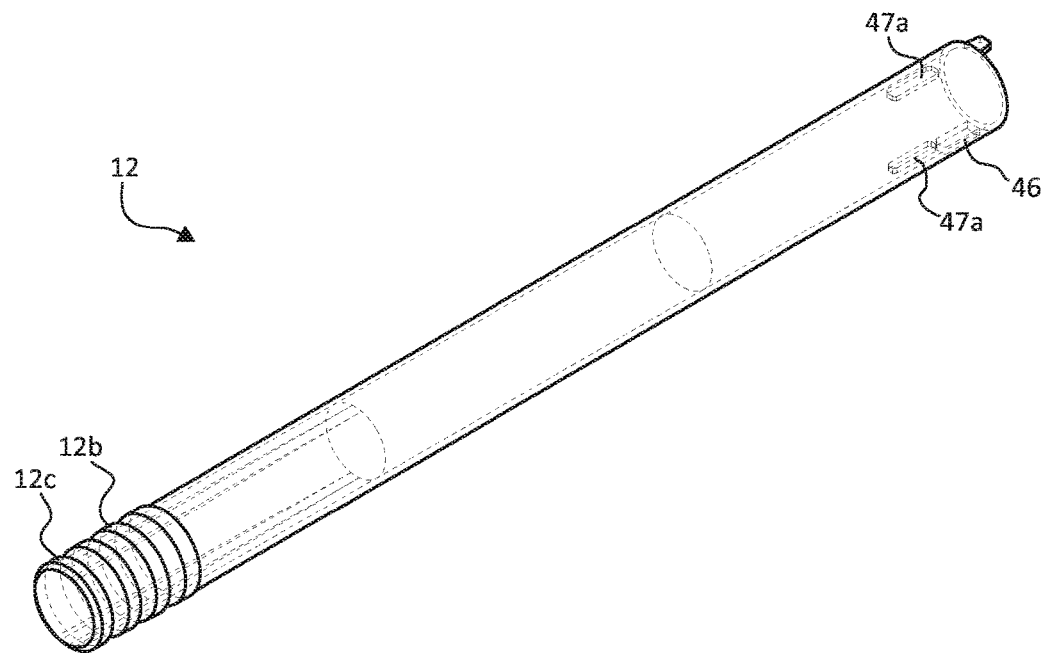
FIG. 13 is a perspective view of a nozzle of the ES pencils of FIGS. 1 and 3 according to the present disclosure.

As shown in FIG. 13, the nozzle 12 has a tubular structure and includes a protrusion 46 disposed at a distal end portion of an outer surface. The protrusion 46 may be inserted into the notch 24 of the upper portion 10a (FIG. 7) to assemble the stationary ES pencil 2 or into the guide rail 26 of the lower portion 10b (FIG. 8) to assembly the telescopic ES pencil 4. This allows for manufacturing the same components, namely upper and lower portions 10a and 10b of the housing 10 to make different variants, namely, the stationary ES pencil 2 and the telescopic ES pencil 4, by simply orienting the nozzle 12 either upwardly to engage the notch 24 or downwardly to engage the guide rail 26.

During assembly of the stationary ES pencil 2, the nozzle 12 is oriented with the protrusion 46 facing the inner surface of the upper portion 10a such that the protrusion 46 is inserted into the notch 24 (FIG. 7). The notch 24 is sized to be substantially the same as the protrusion 46, such that the protrusion 46 is secured therein, thereby preventing the nozzle 12 from moving within the handle housing 10, either rotationally or longitudinally.

During assembly of the telescopic ES pencil 4, the nozzle 12 is oriented with the protrusion 46 facing the inner surface of the lower portion 10b such that the protrusion 46 is disposed within the guide rail 26 (FIG. 8). Engagement of the protrusion 46 within the guide rail 26 limits rotational movement of the nozzle 12 about a main longitudinal axis defined by the housing 10 and allows the nozzle 12 to move only in a longitudinal direction along the main longitudinal axis within the housing 10.

Figure 14:
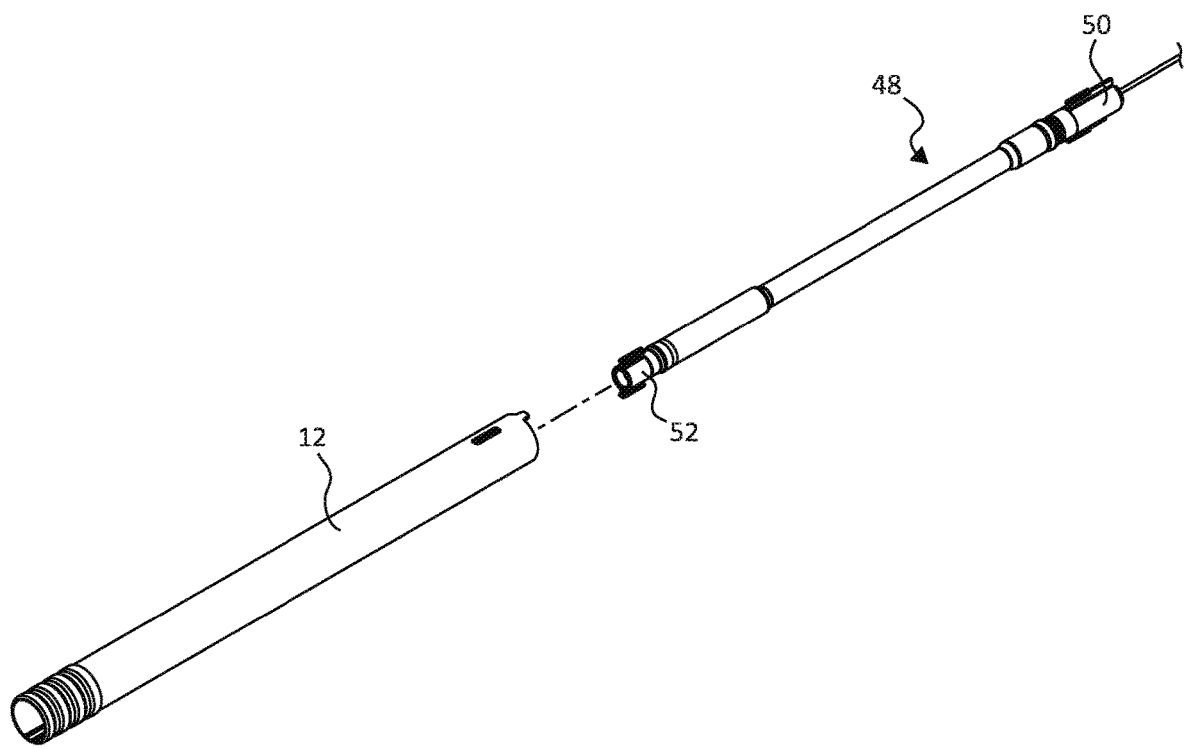
FIG. 14 is a perspective view of a hub assembly separated from the nozzle of the ES pencils of FIGS. 1 and 3 according to the present disclosure.
Figure 15:
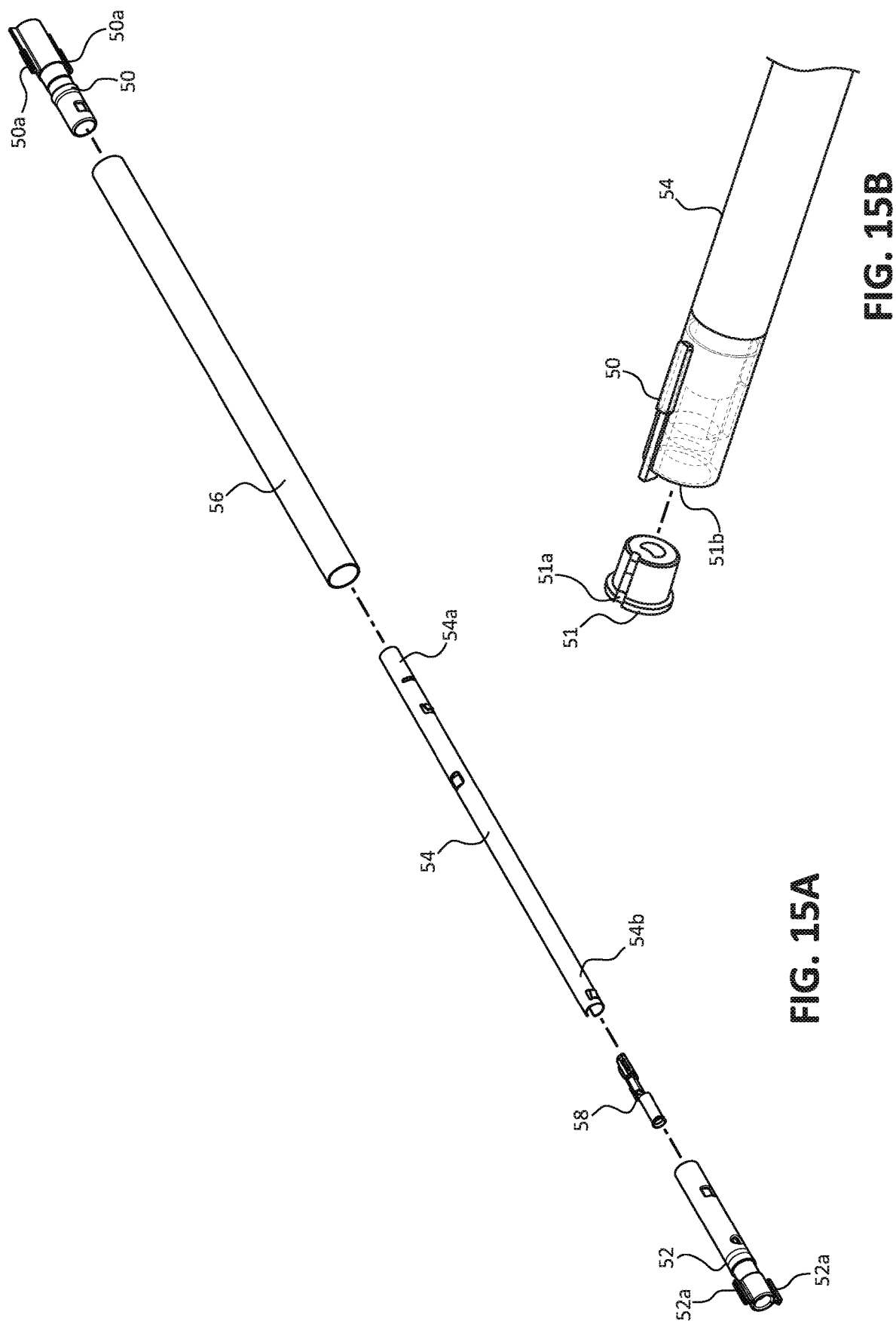
FIG. 15A is a perspective view of the hub assembly of the ES pencils of FIGS. 1 and 3 with parts separated.
FIG. 15B is a perspective view of the proximal end portion of the hub assembly of FIG. 15A.

As shown in FIGS. 14 and 15A, the nozzle 12 also includes a hub assembly 48 disposed therein. The hub assembly 48 provides an electromechanical interface for the electrode 14. The hub assembly 48 is secured within the nozzle 12 by a proximal support 50 and a distal support 52, which are formed from a dielectric material. Each of the proximal support 50 and the distal support 52 includes a pair of flanges 50a and 52a, respectively, which secure the proximal support 50 and the distal supports 52 within the nozzle 12. In embodiments, the nozzle 12 may include a pair of slots 47a (FIG. 13) configured to engage the flanges 52a of the distal support 52. The slots 47a may be sized to prevent longitudinal and lateral movement of the flanges 52a. In addition, the vertical distance between the flanges 52a may be longer than the inner diameter of the nozzle 12, such that the flanges 52a fit within the slots 47a.

With reference to FIG. 15A, which shows the hub assembly 48, the hub assembly 48 includes a cylindrical conductive tube 54 that is inserted into a distal opening of the proximal support 50 and a proximal opening of the distal support 52. Proximal support 50 may further include a plug 51 (see FIG. 15B), which may be received in a proximal end 51b of proximal support 50 to help minimize the ingress of blood, saline, fluids, condensation or other moisture. The conductive tube 54 is coupled to the electrode lead 40, such that the conductive tube 54 conducts electrosurgical energy to the electrode 14. The electrode lead 40 may be crimped or soldered to the conductive tube 54. The electrode lead 40 extends from the distal end portion 34b of the circuit board 34 and is coupled to a proximal end portion 54a of the conductive tube 54 since the conductive tube 54 is coupled to the electrode 14 at its distal end portion 54b. The electrode lead 40 may exit from either a proximal or distal end of the conductive tube 54 and the nozzle 12 and is coupled to the circuit board 34. In embodiments, plug 51 may include a groove 51a configured to fit around the electrode lead 40, allowing for routing electrode lead 40 from the proximal end of conductive tube 54 and through proximal support 50. Alternatively, plug 51 may include an opening therethrough (e.g., centrally located) through which electrode lead 40 may be routed for connecting to circuit board 34. It may be further appreciated that the plug 51 may be located at distal support member 58 and route the electrode lead 40 in a similar manner from that location.

Outside surface of the conductive tube 54 may be insulated by disposing a dielectric material 56 over the conductive tube 54. The dielectric material 56 may be any dielectric polymer applied by dipping, casting, spraying, and other suitable methods. In embodiments, the dielectric material 56 may be a heat-shrink wrap. The dielectric material 56 may be disposed over the conductive tube 54, the proximal support 50, and the distal support 52, thereby securing these components to each other. Additionally, the dielectric material 56 along with the proximal support 50 and distal support 52 insulate the outer surface of the conductive tube 54. The dielectric material 56 prevents smoke and fluid from entering the conductive tube 54 and causing alternative current paths during use of the ES pencil 2 and ES pencil 4.

Figure 16:
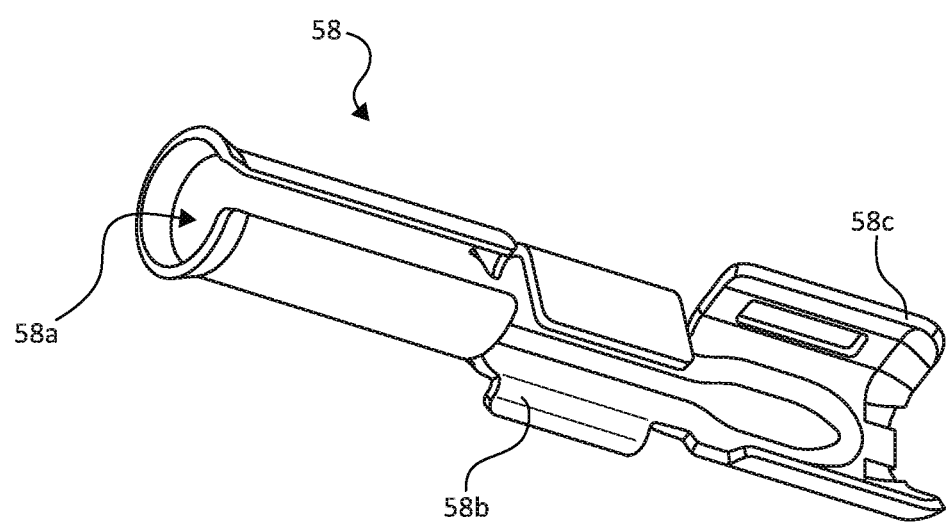
FIG. 16 is a perspective view of an electrode clip for coupling to an electrode of the ES pencils of FIGS. 1 and 3 according to the present disclosure.

The hub assembly 48 also includes an electrode clip 58 that is slidably disposed within the conductive tube 54 and is inserted into the distal end portion 54b. As shown in FIG. 16, the electrode clip 58 includes a socket 58a that receives the proximal portion 14a of the electrode 14 and one or more pairs of contact wings 58b and 58c, which are configured to frictionally engage an inner surface of the conductive tube 54. The contact wings 58b and 58c are spaced apart such that in order to be inserted into the conductive tube 54, the contact wings 58b and 58c may be approximated together and once inserted, the contact wings 58b and 58c spread apart to engage the inner surface of the conductive tube 54. The engagement of the contact wings 58b and 58c provides for an uninterruptable electrical contact between the electrode clip 58 and the conductive tube 54 while allowing for the electrode clip 58 to slide within the conductive tube 54. In addition, the contact wings 58b and 58c also act as friction pads by contacting the conductive tube 54 and securing the electrode clip 58 within the conductive tube 54 unless sufficient force is used to move the electrode clip 58, by moving the electrode 14. In addition, the electrode clip 58 may also rotate within the conductive tube 54, or alternatively, the electrode 14 may rotate within the electrode clip 58, about a longitudinal axis defined by the conductive tube 54.

Figure 17:
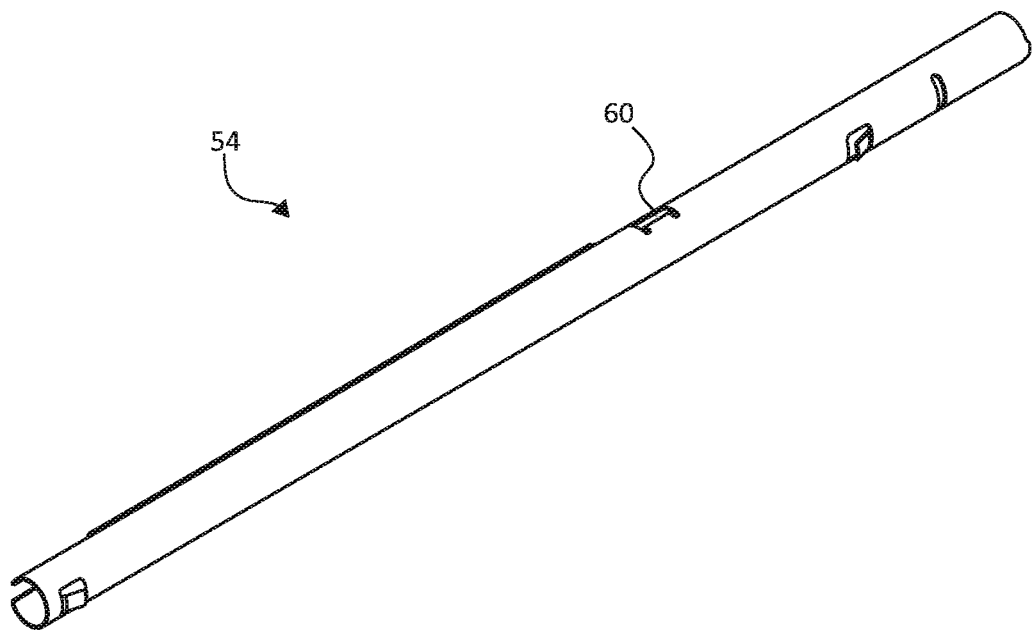
FIG. 17 is a perspective view of a conductive tube of the hub assembly of the ES pencils of FIGS. 1 and 3 according to the present disclosure.

With reference to FIGS. 16 and 17, the conductive tube 54 and the electrode clip 58 may be formed by stamping and rolling sheet metal of suitable gauges. The conductive tube 54 includes a pair of stamped tabs 60, which act as proximal stops for the electrode clip 58 and the distal support 52 acts as a distal stop, thereby limiting the distance that the electrode clip 58 can slide within the conductive tube 54. The tabs 60 may be disposed anywhere along the conductive tube 54 to allow for desired travel of the electrode clip 58.

Thus, in the stationary ES pencil 2, the tabs 60 may be disposed by a distance substantially equal to the length of the electrode clip 58 thereby preventing longitudinal movement the electrode clip 58. In the telescopic ES pencil 2, the tabs 60 may be disposed any distance larger than the length of the electrode clip 58 to accommodate its travel within the conductive tube 54.

The telescopic movement of the electrode 14 is enabled due to the frictional engagement of the electrode 58 with the conductive tube 54. Thus, the frictional engagement of the electrode clip 58 with the electrode 14 is higher than that of the electrode clip 58 with the conductive tube 54. The extension and retraction force required to move the electrode clip 58 can be controlled with the design of the electrode clip 58 such as by adjusting the length of the wings 58b and 58c or the spring rate of the electrode clip 58 by controlling how tightly the electrode clip 58 is wound. Proximal portion 14a of the electrode 14 is seated more securely within the socket 58a of the electrode clip 58 than the engagement of the contact wings 58b and 58c with the conductive tube 54. Thus, when the electrode 14 is moved in a longitudinal direction, the electrode clip 58 slides within the conductive tube 54. The electrode 14 may be removed from the electrode clip 58 by pulling on the electrode 14 in a distal direction until the electrode clip 58 reaches the distal support 52, which acts as a distal stop, and by applying additional force to dislodge the proximal portion 14a of the electrode 14 from the socket 58a of the electrode clip 58.

In the stationary ES pencil 2, the nozzle 12 and the conductive tube 54, which is secured within the nozzle 12, remain stationary within the handle housing 10. In the telescopic variant, the nozzle 12 and the electrode 14 are movable relative to the handle housing 10 and each other. The nozzle 12 may be moved by pulling or pushing on the nozzle 12. Similarly, the electrode 14 may be extended from or retracted into nozzle 12 by pulling or pushing on the electrode 14. However, during extraction or retraction of the electrode 14 the conductive tube 54 remains stationary within the nozzle 12.

It is contemplated that the ES pencil 2 may have a stationary nozzle 12 but a movable electrode 14 by using the conductive tube 54 with the tabs 60 disposed in the manner described above with respect to FIG. 17. It is further contemplated that the ES pencil 4 may have a telescopic nozzle 12 but a stationary electrode 14 but using a conductive tube 54 with the tabs 60 limiting the movement of the electrode clip 58.

Figure 18:
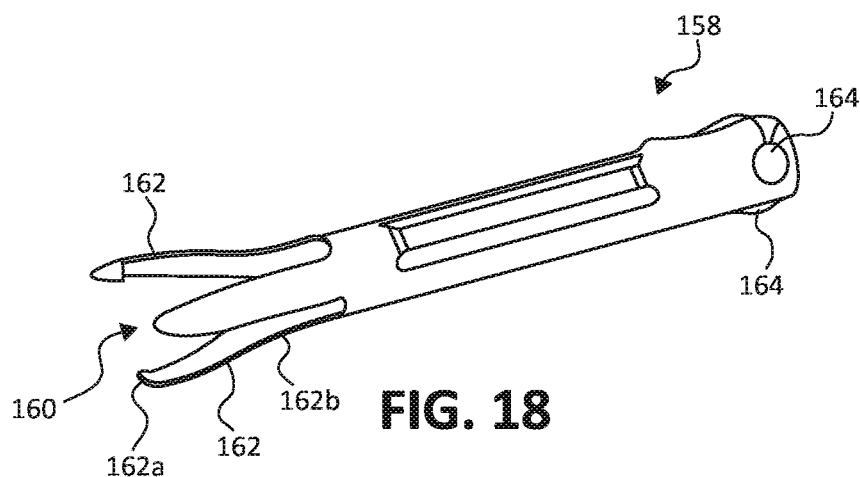
FIG. 18 is a perspective view of an electrode clip according to another embodiment of the present disclosure for coupling to the electrode of the ES pencils of FIGS. 1 and 3.

With reference to FIG. 18, another embodiment of an electrode clip 158 which may be used with the hub assembly 48 of the ES pencil 2 or the ES pencil 4. The electrode clip 158 also includes a lumen 160 for receiving the electrode 14. The electrode clip 158 also includes a plurality of prongs 162 disposed at a distal portion of the electrode clip 158 and a plurality of surface features 164 disposed at a proximal portion of the electrode clip 158. The prongs 162 include a pointed end 162a and a curved portion 162b.

Figure 19:
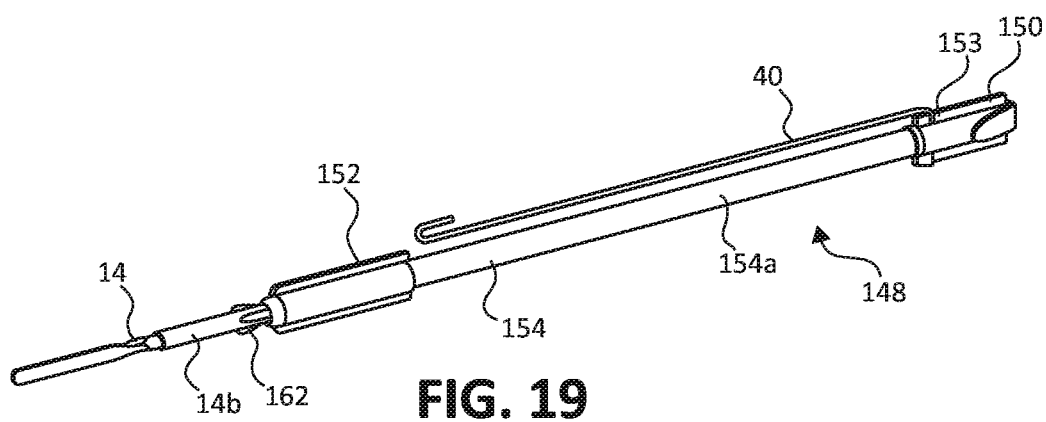
FIG. 19 is a perspective view of a hub assembly according to another embodiment of the present disclosure for coupling to the electrode of the ES pencils of FIGS. 1 and 3.

With reference to FIG. 19, another embodiment of a hub assembly 148, which may be used interchangeably with any of the described embodiments, such as the electrode clip 58 or electrode clip 158, the ES pencil 2 or the ES pencil 4. The hub assembly 148 is substantially similar to the hub assembly 48 and includes a conductive tube 154, which has a faceted structure. In embodiments, the conductive tube 154 may have any number of facets 154a, such as hexagonal, octagonal, etc. The electrode clip 58 or the electrode clip 158 can move longitudinally and rotationally within the conductive tube 154. The facets 154a of the conductive tube 154 allow for incremental rotation of the electrode clip 58 about a longitudinal axis defined by the conductive tube 154 by requiring a higher amount of torque to rotate the electrode 14 and the electrode clip 58 or the electrode clip 158 to each corner between the facets 154a of the conductive tube 154.

The hub assembly 148 also includes a proximal support 150 and a distal support 152, which may be formed by overmolding the proximal support 150 and the distal support 152 over the conductive tube 154. In embodiments, the proximal support 50 and the distal support 52 may be overmolded over the conductive tube 54 as well. The distal support 152 may include an opening 153 for passage of the electrode lead 40 therethrough.

With reference to FIG. 19, as the electrode 14 is inserted into the lumen 160 of the electrode clip 158, the electrode clip 158 is inserted into a conductive tube 154, and a proximal end of the electrode 14 engages the curved portions 162b of the prongs 162 thereby compressing the prongs 162 and moving the pointed ends 162a to pierce an insulative coating 14b of the electrode 14, thereby securing the electrode 14 within the electrode clip 158. The insulative coating 14b may be any dielectric polymer applied by dipping, casting, spraying, and other suitable methods. In embodiments, the insulative coating 14b may be a heat-shrink wrap. The surface features 164 may be bumps, wings, or any other structures configured to engage the conductive tube 154. Similar to the contact wings 58b and 58c, engagement of the surface features 164 provides for an uninterruptable electrical contact between the electrode clip 158 and the conductive tube 54 while allowing for the electrode clip 158 to slide within the conductive tube 154.

In addition, the surface features 164 also act as friction pads by contacting the conductive tube 54 and securing the electrode clip 58 within the conductive tube 154 unless sufficient force is used to move the electrode clip 158, by moving the electrode 14. Since the electrode 14 is secured to the electrode clip 158 via the prongs 162, the electrode clip 158 may be moved within the conductive tube 54 by pulling or pushing on the electrode 14.

Figure 20:
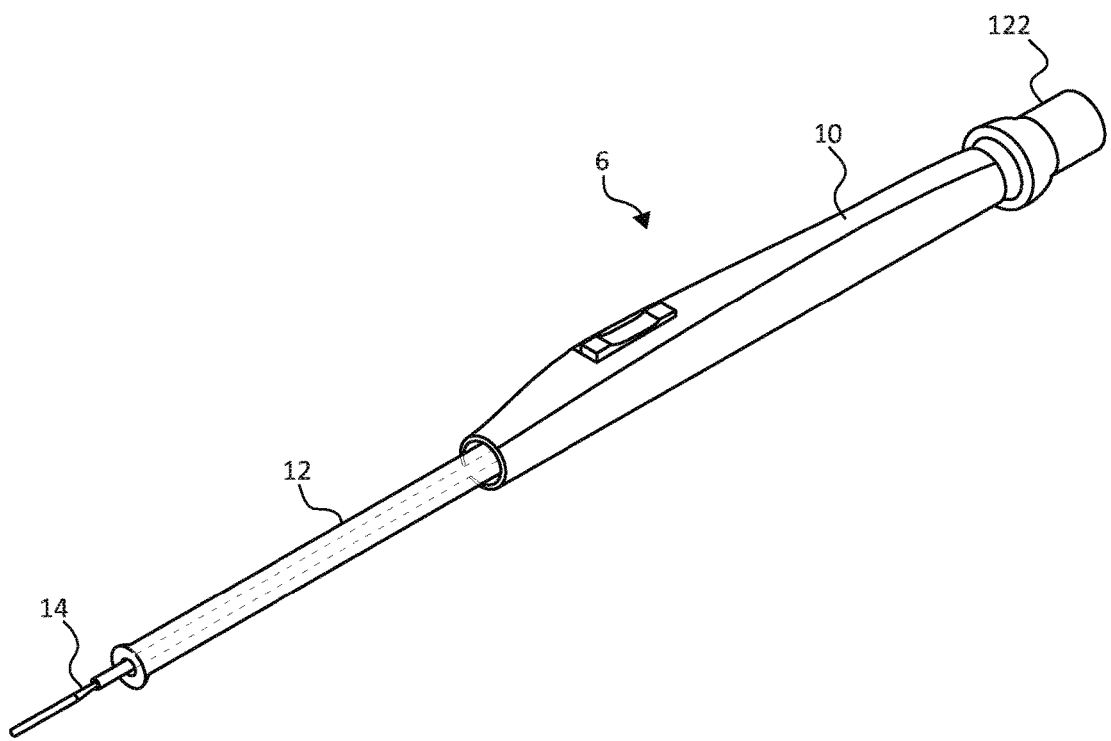
FIG. 20 is a perspective view of a smoke evacuation ES pencil according to a further embodiment of the present disclosure.
Figure 21:
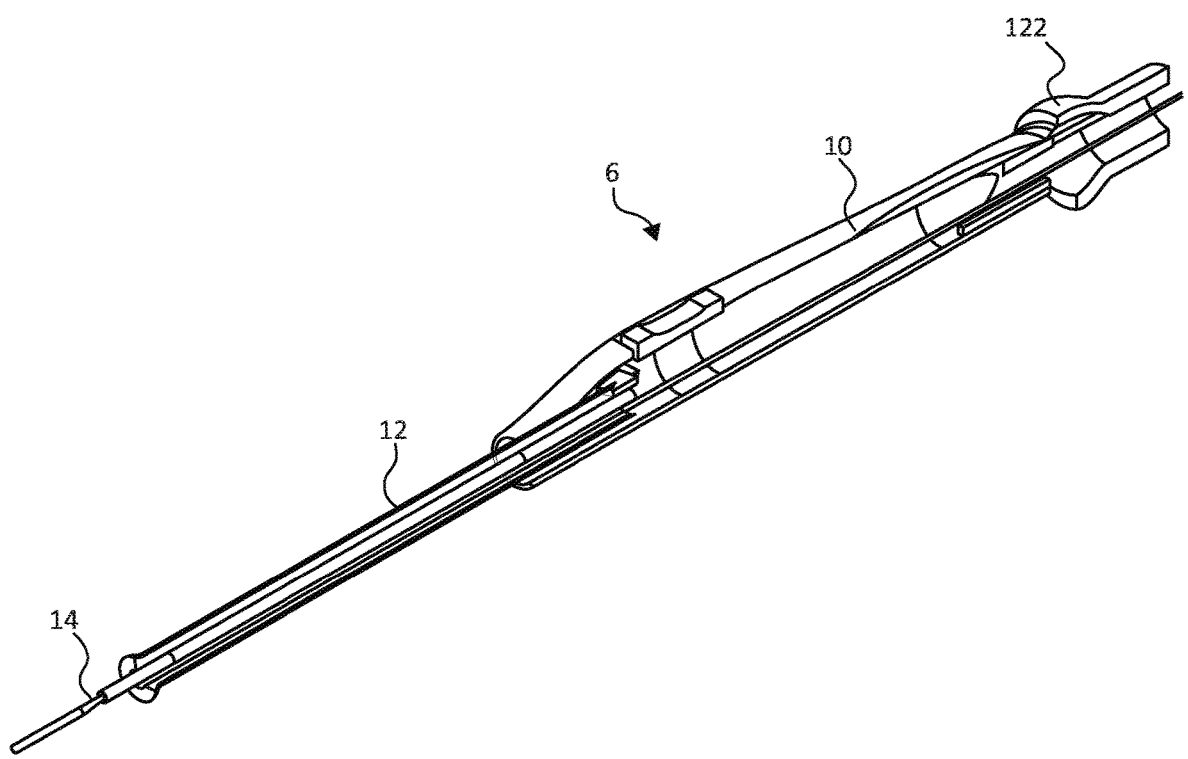
FIG. 21 is a perspective, cross-sectional view of the ES pencil of FIG. 20.
Figure 22:
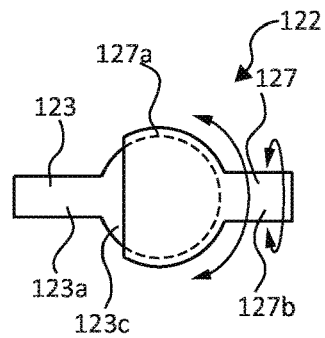
FIG. 22 is a side view of a swivel connector according to another embodiment of the present disclosure.

With reference to FIGS. 20 and 21, another embodiment of an ES pencil 6 is shown and includes the telescopic nozzle 12 as described above with respect to ES pencil 4. In other embodiments, the ES pencil 6 may have a stationary nozzle 12. The ES pencil 6 is substantially similar to the ES pencils 2 and 4 and includes the same components described above.

With reference to FIG. 20, the swivel connector 122 includes a distal joint 123 and a proximal joint 127. The swivel connector 122 is a ball joint with the distal joint 123 having a tubular section 123a configured to be inserted into the tubular member 20 of the upper portion 10a such that the distal joint 123 can rotate about a first longitudinal axis defined by the distal joint 123. The distal joint 123 includes an outer curved surface 123c configured to engage an inner curved surface 127a of the proximal joint 127. The proximal joint 127 also includes a tubular section 127b configured to couple to the tubing 15. The ball joint design of the swivel connector 122 allows the proximal joint 127 to rotate and pivot relative to the distal joint 123 in two planes at the same time.

Figure 23:
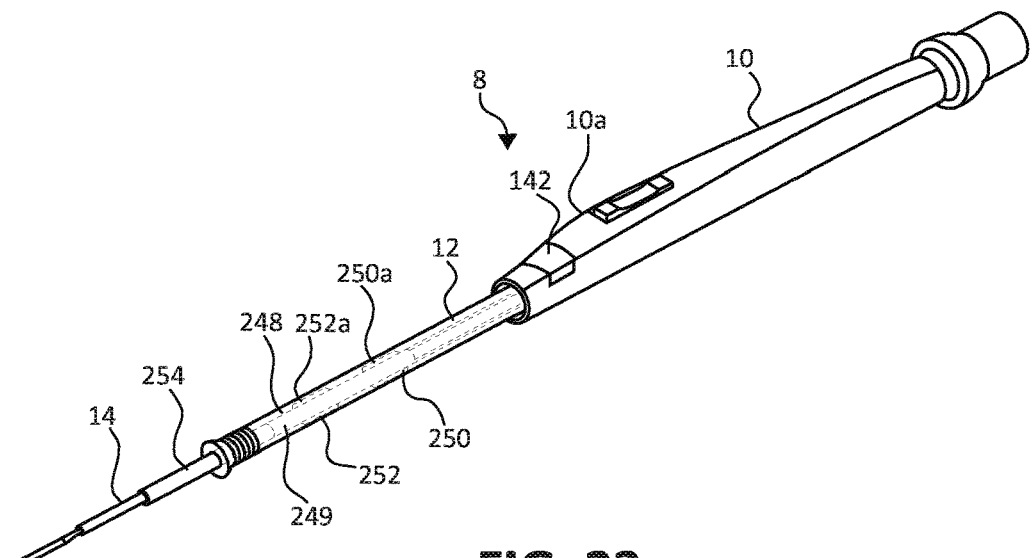
FIG. 23 is a perspective view of a smoke evacuation ES pencil according to an embodiment of the present disclosure.
Figure 24:
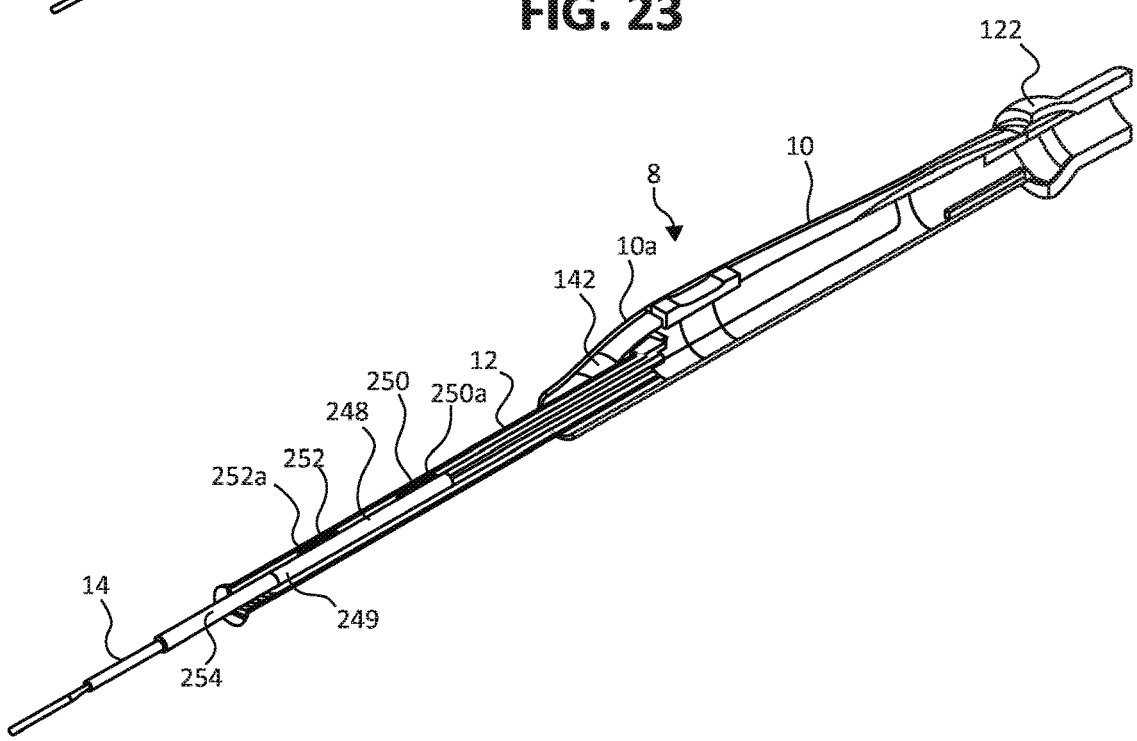
FIG. 24 is a perspective, cross-sectional view of the ES pencil of FIG. 23.

With reference to FIGS. 23 and 24, a further embodiment of an ES pencil 8 is shown. The ES pencil 8 is substantially similar to the ES pencil 2, 4, and 6 in that the nozzle 12 and the electrode 14 may be stationary or movable as described above. The ES pencil 8 includes a friction pad 142 disposed in the upper portion 10a of the handle housing 10. The friction pad 142 may be formed from an elastomeric, conformable material such as silicone rubber. Suitable silicone rubbers include room temperature vulcanization (RTV) silicone rubbers; high temperature vulcanization (HTV) silicone rubbers and low temperature vulcanization (LTV) silicone rubbers. These rubbers are known and readily available commercially such as SILASTIC® 735 black RTV and SILASTIC® 732 RTV, both from Dow Corning; and 106 RTV Silicone Rubber and 90 RTV Silicone Rubber, both from General Electric. Other suitable silicone materials include the silanes, siloxanes (e.g., polydimethylsiloxanes) such as, fluorosilicones, dimethylsilicones, liquid silicone rubbers such as vinyl crosslinked heat curable rubbers or silanol room temperature crosslinked materials, and the like.

The friction pad 142 may be secured or simply placed within the upper portion 10a to allow for the friction pad 142 to contact the nozzle 12 by resting on the nozzle 12. The friction pad 142 contacts and secures the nozzle 12 within the housing 10 unless sufficient force is used to move the nozzle 12, thereby modulating the amount of force needed to move the nozzle 12 longitudinally. The friction pad 142 may be incorporated into any of the above embodiments of the ES pencil 2, 4, and 6 and may be used in conjunction with or in place of the wings 42 of the midframe 28. The friction pad 142 may also be positioned at any longitudinal location within the housing 10 such as in a distal portion as shown in FIGS. 23 and 24 or at a proximal portion.

Nozzle 12 and electrode 14 are independently extendable and retractable, each in a manner as set forth above. To facilitate such independent movement, the forces required to extend and retract each of the nozzle 12 and electrode 14 are designed such that one of the nozzle 12 or electrode 14 is extendable or retractable at a lower force than the other. More specifically, electrode 14 may be extended or retracted by applying a first force $F_1$ that is less than the force $F_2$ required to extend or retract nozzle 12. As such, a user may grasp electrode 14 and apply force $F_1$ to extend/retract electrode 14 without affecting the absolute position of nozzle 14. Similarly, user may grasp nozzle 12 and apply a force $F_2$ to extend or retract it without affecting the position of nozzle 12 relative to the tip of electrode 14. It is further understood that the relationship of forces between electrode 14 and nozzle 12 could be reversed such that $F_2$ is less than $F_1$. In other words, forces $F_1$ and $F_2$ are different, allowing for separate movement of the electrode 14 and the nozzle 12 relative to each other and the housing 10. In addition, electrode 14 has an extraction force $F_3$ required to remove electrode 14 from the device. In embodiments, electrode extraction force $F_3$ may be greater than both the electrode movement force $F_1$ and nozzle movement force $F_2$. In embodiments, the movement force $F_1$ for moving the electrode 14 may be from about 0.15 pounds per inch sq. (lbs/in$^2$) to about 3 lbs/in$^2$, the movement force F2 for moving the nozzle 14 may be from about 0.5 lbs/in$^2$ to about 7 lbs/in$^2$, and electrode extraction force $F_3$ may be from about 2 to about 10 lbs/in$^2$.

With continued reference to FIGS. 23 and 24, the ES pencil 8 may also include a hub assembly 248 that is movable within the nozzle 12 allowing for the electrode 14 to move relative to the nozzle 12. The hub assembly 248 includes an outer carrier 249 having a proximal support 250 and a distal support 252, which may be assembled as separate components like the proximal support 50 and the distal support 52 or may be overmolded like the proximal support 150 and distal support 152. The outer carrier 249 may be formed from a dielectric material and includes a lumen therethrough.

With continued reference to FIGS. 23 and 24, the proximal support 250 and the distal support 252 include flanges

250a and 252a, respectively, which contact the inner surface of the nozzle 12. The flanges 250a and 252a secure the outer carrier 249 within the nozzle 12 while allowing for the outer carrier 249 to be moved longitudinally within the nozzle 12. Additionally, the ES pencil 8 also includes a conductive tube 254 slidably disposed within the outer carrier 249. The conductive tube 254 has an outer surface insulated by depositing a dielectric material (e.g., dielectric material 56) thereon. The electrode 14 may be slidably disposed within conductive tube 254 in a similar manner as described above with respect to the conductive tubes 54 and 154 by using the electrode clips 58 and 158. The combination of the electrode 14, the conductive tube 254, and the outer carrier 249 provides for a telescopic mechanism with each of these components being movable relative to each other and within the nozzle 12.

In embodiments, first frictional engagement between the electrode 14 and the conductive tube 254 may be the same as second frictional engagement between the conductive tube 254 and the outer carrier 249 and third frictional engagement between the outer carrier 249 and the nozzle 12. As used herein, "frictional engagement" denotes the force needed to move one component relative to another (e.g., electrode 14 relative to the conductive tube 254). In further embodiments, the first, second, and third frictional engagements may progressively increase or decrease, such that the first frictional engagement is higher than the second frictional engagement, which is in turn, higher than the third frictional engagement, or vice versa.

It will be understood that various modifications may be made to the embodiments of the presently disclosed smoke evacuation ES pencils. Therefore, the above description should not be construed as limiting, but merely as exemplifications of embodiments. Those skilled in the art will envision other modifications within the scope and spirit of the present disclosure.

What is claimed is:

1. An electrosurgical pencil comprising:
   a handle housing having a proximal end portion and a distal end portion, the handle housing defining a first lumen therethrough;
   a nozzle disposed within the first lumen and defining a second lumen, the nozzle being movable relative to and within the handle housing and extending distally past the distal end portion of the handle housing;
   a swivel connector coupled to the proximal end portion of the handle housing, the swivel connector configured to couple to a suction source;
   a hub assembly fixed within the second lumen of the nozzle such that the hub assembly longitudinally moves with a longitudinal movement of the nozzle relative to the handle housing, the hub assembly including a tube configured to couple to a source of electrosurgical energy; and
   an electrode slidably disposed within the tube, the electrode being movable relative to and within the tube; and
   an electrode clip slidably disposed within the tube, the electrode clip being movable relative to and within the tube.

2. The electrosurgical pencil according to claim 1, wherein the hub assembly includes a proximal support disposed over a proximal end portion of the tube and a distal support disposed over a distal end portion of the tube.

3. The electrosurgical pencil according to claim 2, wherein the proximal support and the distal support are formed from a dielectric material.

4. The electrosurgical pencil according to claim 1, wherein the hub assembly further includes a dielectric material disposed over the tube.

5. The electrosurgical pencil according to claim 4, wherein the dielectric material is a heatshrinkable wrap.

6. The electrosurgical pencil according to claim 2, wherein each of the proximal support and the distal support includes a plurality of flanges configured to secure each of the proximal support and the distal support within the nozzle.

7. The electrosurgical pencil according to claim 2, wherein the tube includes a proximal stop member and longitudinal movement of the electrode clip is limited by the distal support and the proximal stop member.

8. The electrosurgical pencil according to claim 1, wherein the electrode clip includes a socket configured to receive a proximal end portion of the electrode and a pair of contact wings configured to contact an inner surface of the tube.

9. The electrosurgical pencil according to claim 1, wherein the electrode clip includes a plurality of prongs disposed at a distal portion of the electrode clip and a plurality of surface features disposed at a proximal portion of the electrode clip, the surface features being configured to contact an inner surface of the tube.

10. The electrosurgical pencil according to claim 1, further comprising a midframe disposed within the handle housing and over the nozzle.

11. The electrosurgical pencil according to claim 10, wherein the midframe includes a pair of wings configured to frictionally engage the nozzle.

12. The electrosurgical pencil according to claim 1, wherein the handle housing includes an upper portion having a switch opening and a lower portion.

13. The electrosurgical pencil according to claim 12, further comprising a circuit board including at least one switch and a rocker disposed through the switch opening, the rocker configured to engage the at least one switch.

14. The electrosurgical pencil according to claim 1, wherein the proximal end portion of the handle housing includes a tubular connector.

15. The electrosurgical pencil according to claim 14, wherein the swivel connector includes:
   a distal joint coupled to the tubular connector and rotatable about a first longitudinal axis defined by the tubular connector; and
   an intermediate joint coupled to the distal joint and pivotable about an axis that is perpendicular to the first longitudinal axis.

16. The electrosurgical pencil according to claim 15, wherein the swivel connector further includes:
   a proximal joint coupled to the intermediate joint and rotatable about a second longitudinal axis defined by the intermediate joint.

17. The electrosurgical pencil according to claim 15, wherein the distal joint includes a pair of opposing pins and the intermediate joint includes a pair of opposing openings configured to engage the pair of opposing pins.

18. The electrosurgical pencil according to claim 15, wherein the distal joint includes an outer curved surface and the intermediate joint includes an inner curved surface, the outer curved surface include a raised surface configured to limit pivoting movement of the intermediate joint.

19. An electrosurgical pencil comprising:
   a handle housing having a proximal end portion and a distal end portion, the handle housing defining a first lumen therethrough, the proximal end portion of the handle housing including a tubular connector;
a nozzle disposed within the first lumen and defining a second lumen, the nozzle being movable relative to and within the handle housing and extending past the distal end portion of the handle housing;
a swivel connector coupled to the proximal end portion of the handle housing, the swivel connector configured to couple to a suction source, wherein the swivel connector includes:
   a distal joint coupled to the tubular connector and rotatable about a first longitudinal axis defined by the tubular connector;
   an intermediate joint coupled to the distal joint and pivotable about an axis that is perpendicular to the first longitudinal axis; and
   a proximal joint coupled to the intermediate joint and rotatable about a second longitudinal axis defined by the intermediate joint;
a hub assembly securedly disposed within the second lumen, the hub assembly including a tube configured to couple to a source of electrosurgical energy;
an electrode slidably disposed within the tube, the electrode being movable relative to and within the tube.

* * * * *